United States Patent [19]
Carbonell et al.

[11] Patent Number: 5,494,803
[45] Date of Patent: Feb. 27, 1996

[54] IMMUNODIAGNOSTIC ASSAY USING LIPOSOMES CARRYING LABELS THEREOF ON OUTER LIPOSOME SURFACE

[75] Inventors: Ruben G. Carbonell; Peter K. Kilpatrick, Cary; Matthew A. Jones, Raleigh; Anup K. Singh, both of Raleigh, all of N.C.

[73] Assignee: North Carolina State University, Raleigh, N.C.

[21] Appl. No.: 273,280

[22] Filed: Jul. 11, 1994

Related U.S. Application Data

[63] Continuation of Ser. No. 795,910, Nov. 19, 1991, abandoned.

[51] Int. Cl.[6] .................... G01N 33/543; G01N 33/58; G01N 21/62
[52] U.S. Cl. ................ 435/7.92; 435/7.93; 435/7.94; 436/518; 436/172; 436/165; 436/829; 422/57; 422/82.11
[58] Field of Search .................. 435/7.92, 7.93, 435/7.94, 188, 808, 968; 436/518, 165, 172, 829; 422/57, 68.1, 82.05, 82.11

[56] References Cited

U.S. PATENT DOCUMENTS

| | | | |
|---|---|---|---|
| 4,605,630 | 8/1986 | Kung et al. | 436/511 |
| 4,707,453 | 11/1987 | Wagner et al. | 436/501 |
| 4,743,560 | 5/1988 | Campbell et al. | 436/501 |
| 4,762,915 | 8/1988 | Kung et al. | 530/405 |
| 4,880,752 | 11/1989 | Keck et al. | 435/7 |
| 4,913,902 | 4/1990 | Kilpatrick et al. | 424/85.8 |
| 4,978,625 | 12/1990 | Wagner et al. | 436/518 |
| 5,000,960 | 3/1991 | Wallach | 424/430 |
| 5,045,478 | 9/1991 | Wagner et al. | 436/501 |

OTHER PUBLICATIONS

J. Conner et al., *Biochemistry* 26, 5099–5105 (1987).
H.-N. Dao et al., *Analytical Biochemistry*, 196, 46–53 (1991).
T. D. Health et al., *Covalent Attachment of Horseradish Peroxidase to the Outer Surface of Liposomes*, 599 Biochimica et Biophysica Acta 42 (1980).
A. Huang et al., *Immunoliposome Labeling: A Sensitive and Specific Method for Cell Surface Labeling*, 46 J. Immunological Methods 141 (1981).

*Primary Examiner*—Toni R. Scheiner
*Assistant Examiner*—Nancy J. Parsons
*Attorney, Agent, or Firm*—Bell, Seltzer, Park & Gibson

[57] ABSTRACT

Competitive and sandwich-type immunodiagnostic assays can be configured by use of liposomes carrying detectible markers (e.g., fluorophores) or catalysts thereof (e.g., enzymes) on the outer liposome surface. The liposome also contains at least one antigen or antibody allowing it to bind to a complementary, immobilized antibody or antigen on a support.

18 Claims, 14 Drawing Sheets

IMMUNODIAGNOSTIC ASSAY USING LIPOSOMES CARRYING LABELS THEREOF ON OUTER LIPOSOME SURFACE

This is a continuation of application Ser. No. 07/795,910 filed on Nov. 19, 1991 abandoned.

BACKGROUND OF THE INVENTION

A variety of immunodiagnostic assays are known to persons of ordinary skill in the art. For example, in the competitive solid phase immunoassay architecture, labeled tracer antigen, for instance, competes with unknown sample antigen for a limited number of antibody binding sites immobilized on a solid phase support. The tracer or detectible marker that is bound and quantitated is inversely proportional to the unknown analyte. In the two-site immunometric or "sandwich" architecture, for instance, high molecular mass analytes form a complex between immobilized antibody and tracer antibody with the signal being directly proportional to analyte concentration. These types of detectible markers (or tracers) which are employed with such immunodiagnostic assays can be varied and include radioisotopes, fluorescent materials, enzymes (which for purposes of the present invention are classified as catalysts for a detectible marker which is, for example, visually or spectrophotometrically perceivable), and the like. The term "label" is used herein to generically cover the aforementioned markers and catalysts (e.g., enzymes). One promising approach is to immobilize the antibody or antigen, as appropriate, in the particular type of assay desired on a waveguide material through which light can be appropriately directed to generate an evanescent wave adjacent the interface between the bulk solution containing the unknown to be measured and the waveguide surface. It is within this evanescent wave field that the detectible marker can be visually detected and measured.

Liposomes have been used as one component of prior art immunodiagnostic assays. In most cases, they have been used to entrap fluorescent dyes, enzymes, radioactive compounds, and the like inside the vesicles with either subsequent lysis or disruption of the vesicles to release the signal enhancing compounds. For example, U.S. Pat. No. 4,743,560 to R. L. Campbell describes a solid phase assay which features a liposome component which includes a detectible marker which is not visible.

U.S. Pat. No. 4,707,453 describes a solid phase assay in which vesicles are used which are formed, in part, from an amphiphilic chelating agent whereby a detectible metal marker can be complexed to the vesicle. The reference indicates that the detectible marker is external to the bilayer of the vesicle or sac in the sense of being both inside and outside the sac. The metal markers which are described for use in this patent are attached to the liposome substrate via chelating agents by means of a non-covalent bond which can dissociate.

A. Huang et al. in Journal of Immunological Methods, 46 (1981) 141–151, describes labeling of liposomes with ligands (i.e., antibodies) and fluorescent groups. This publication indicates that the immunoliposome labeling technique described therein was potentially very versatile without any specific description of an immunodiagnostic assay protocol or architecture for implementation. Also, the method for immobilizing proteins to vesicles which is described by Huang et al. requires modification of the protein by attachment of hydrophobic ligands prior to vesicle formation. When such a procedure is used, one runs the risk of precipitating the protein and, for example, of incorporating the protein incorrectly oriented on the vesicle bilayer as the vesicles are formed.

Another prior art reference which relates to vesicles and their use in an assay is U.S. Pat. No. 5,045,478 which, at Col. 4, lines 14–33, indicates that although the detectable marker used in such an assay is generally enclosed or encapsulated within the sac or vesicle, the vesicle "may be derivatized with the marker in a manner similar to derivatizing the sac with a ligand" (Col. 4, lines 17–18). This reference, however, clearly indicates a concern for "premature rupturing" (Col. 4, line 65) of such sacs and indicates that, in general, the marker is to be released from the sac (see, for example, Col. 5, lines 8–20).

SUMMARY OF THE INVENTION

The present invention, in one embodiment, is a competitive assay for measuring the amount of an unknown antigen or antibody, respectively. The assay comprises (a) a plurality of immobilized antibodies or antigens, respectively, bonded to a support and in contact with the solution; and (b) a plurality of liposomes, in the solution with the unknown, carrying (i) a plurality of labels, e.g., detectible markers or catalysts thereof, covalently bonded to the outer surface of each liposome, and (ii) at least one antigen or antibody, respectively, also covalently bonded to the outer surface of each liposome, which antigen or antibody is complementary to the immobilized antibodies or antigens, respectively, so as to bind the liposomes to at least one immobilized antibody or antigen, respectively, on the support and allow for the detection of the label, e.g., detectible markers or catalysts thereof, adjacent the support without rupture of the liposomes and thereby provide a competitive measurement of the amount of unknown antigen or antibody in the bulk solution.

In the sandwich assay embodiment of the present invention, the assay comprises (a) a plurality of immobilized antibodies or antigens, respectively, bonded to a support which are complementary to the unknown antigen or antibody, respectively, and which are in contact with the solution; and (b) a plurality of liposomes, in the solution with the unknown, carrying (i) a plurality of labels, e.g., detectible markers or catalysts thereof, covalently bonded to the outer surface of each liposome, and (ii) at least one antibody or antigen, respectively, also covalently bonded to the outer surface of each liposome, which is also complementary to the unknown antigens or antibodies, respectively, so as to indirectly bind the liposomes to the immobilized antibodies or antigens, respectively, on the support with the unknown antigen or antibody lying therebetween so as to allow for the detection of the labels, e.g., detectible markers or catalysts thereof, adjacent the support without rupture of the liposomes and thereby provide a direct measurement of the amount of the unknown antigen or antibody in the bulk solution.

The present invention, in yet another embodiment, are novel liposomes which are useful in the previously described assays which have either antigen or antibody on their outer surfaces and enzyme as the label.

DESCRIPTION OF THE DRAWINGS

This invention is further understood by reference to the Drawings wherein.

DETAILED DESCRIPTION OF THE INVENTION

Figure 1:
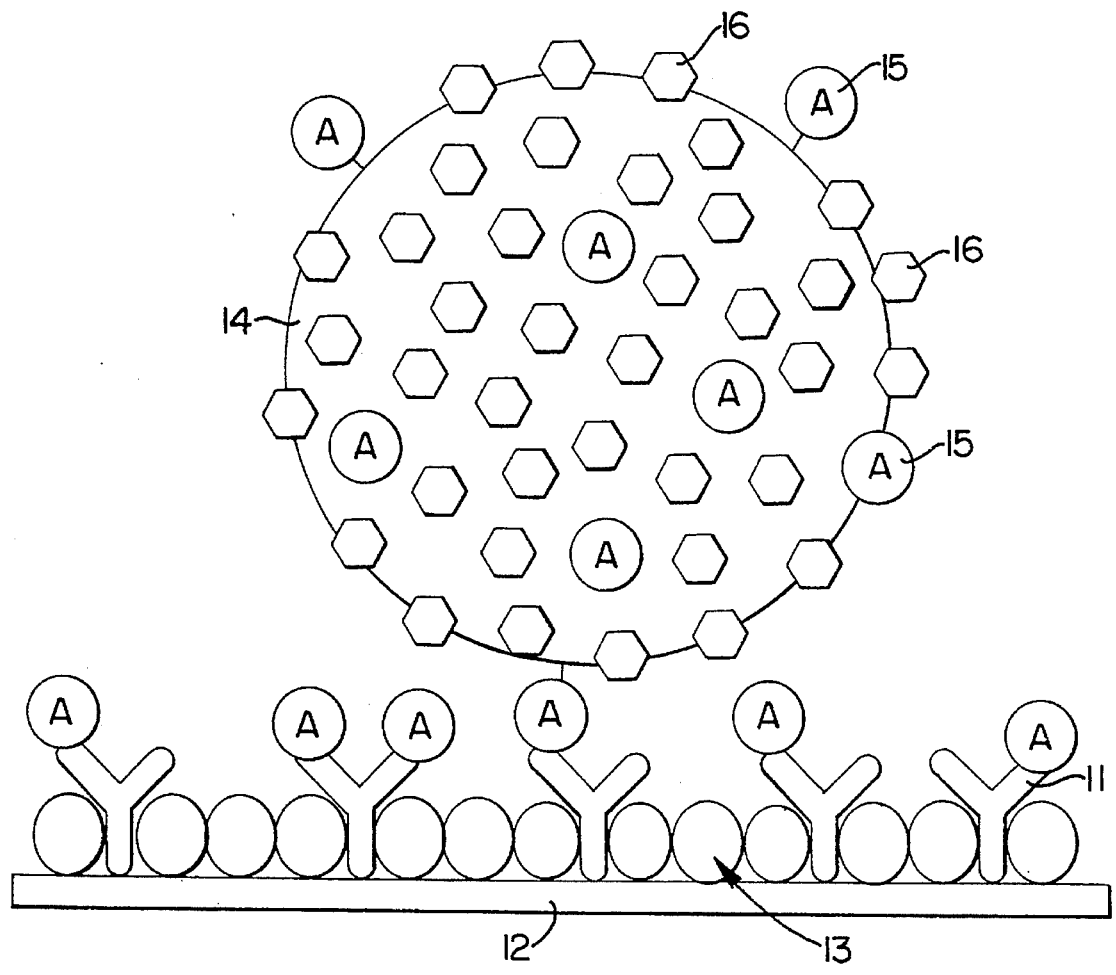
FIG. 1 is a schematic view of a unilamellar liposome with covalently-attached labels and antigens for use in a competitive assay.

The immunodiagnostic assay procedures described herein comprise, as an essential element or component, a liposome comprising lipid wall portions having covalently bonded thereto, on the outer surface thereof, either antigen or antibody, depending upon the type of assay configuration desired (either competitive or "sandwich") and either a label, i.e., a detectible marker (e.g., a fluorophore) or a catalyst for such a marker (e.g., an enzyme). FIG. 1 illustrates the generic configuration for such liposomes in either a competitive fluoroimmunoassay or enzyme-linked immunoassay, for determining unknown in bulk solution. In each assay configuration, an antibody 11 is immobilized on a support 12 which, optionally, can have portions of its surface appropriately blocked, e.g., with bovine serum albumen 13, to substantially reduce or eliminate non-specific binding during the immunoassay procedure. The top portion of the support 12, the immobilized antibody 11, and other components to be described below are bathed by the bulk solution (not shown) containing the unknown to be analyzed. The liposome body 14 (which can be a lipid bilayer) has a plurality of antigens 15 covalently bonded to its outer surface thereof (complementary to the immobilized antibody 11 so as to bind thereto by antigen-antibody binding) and a plurality of labels 16 which can be directly detectible markers (e.g., fluorophores) or catalysts (e.g., enzymes) for a detectible marker. The support 12 can be an optical waveguide through which light can be shone to produce an evanescent wave adjacent the interface between the junction between the waveguide and the bulk solution in a manner known with conventional fluorometric immunoassays, not containing the novel liposome component described herein, so as to allow for detection of a visually detectible marker in the evanescent wave region.

The configuration shown in FIG. 1 is for a competitive-type assay where unknown antigen is to be detected. Reversal of the respective antibody 11 and antigen 15 components to suitable antigen and antibody components, respectively, is possible if unknown antibody in bulk solution is to be measured.

An alternative arrangement is a "sandwich" type immunoassay for antigen, for example, in bulk solution where the measurement of the detectible marker (either carried by the liposomes or measured via catalysts carried by the liposomes) provides a direct measure of the unknown in solution. In the sandwich configuration, antibody can be immobilized on the support which is complementary to the unknown antigen and the liposomes carry complementary antibodies as well (along with the detectible markers or catalysts thereof). In such a configuration, the unknown antibody will become "sandwiched" between the immobilized antibody and the liposome-carried antibodies. An alternative arrangement to measure antibody in bulk solution is to immobilize antigen on the support and provide complementary antigens on the liposomes.

In either the sandwich or competitive assays, the appropriate antigen or antibody is immobilized on the support, the liposomes, appropriately configured with either antigen or antibody (depending on the type of assay) and either detectible marker or catalyst (depending upon whether the marker is desired on the liposome itself or in the environment adjacent the liposome so as to be amplified/detected, as in the case of ELISA technology), are then added to the bulk solution to either compete with the unknown for antibody/antigen immobilized on the support or to act to sandwich the unknown between the immobilized antibody/antigen and an antibody/antigen moiety or moieties carried by the liposome.

A rather wide range of surfactants are available for vesicle preparation and chemical modification can be used to prepare the liposomes (or vesicles) useful for the present invention. The person of ordinary skill in the art may select suitable materials from the di- and trialkyl quaternary ammonium salts, the dialkyl phosphates, the dialkyl glycerols, and the dialkyl glycolipids to name just a few. One example of a general overview of the different types of chemistry useful in preparing such liposomes is given, for example, by H. Ringsdorf et al., Agnew. Chem. Int. Ed. Engl., 27, 113 (1988).

The liposomes, for example, used herein may be formed from: (a) a phospholipid (e.g., distearoylphosphatidyl choline) which provides the basic structure; (b) a phospholipid conjugated with a label, for example, a fluorescent label as a directly detectable marker (e.g., dipalmitoylphosphatidyl ethanolamine covalently modified by attachment to fluorescein isothiocyanate), or catalysts thereof (enzymes); (c) a phospholipid with a reactive end group (e.g., dipalmitoylphosphatidyl ethanolamine) for covalent attachment of a desired antigen or antibody; and (d) optionally, cholesterol for temperature and chemical stability.

In general terms, it is well known to persons of ordinary skill in the art how appropriate ligands can be coupled to the liposomes to be used herein. U.S. Pat. No. 5,000,960 provides a general review of coupling techniques at Col. 1, lines 26–56 which might be employed. Other references which give a summary of the technology available are: L. Leserman et al., Ligand Targeting of Liposomes, in Liposomes: from Biophysics to Therapeutics, M. J. Ostro, ed., Marcel Dekker, 1987; F. J. Martin et al., Liposomes: A Practical Approach, R. R. C. New, ed., IRL Press, Oxford University Press, 1990; and V. P Torchilin, Immobilization of Specific Proteins on Liposome Surface Systems for Drug Targeting, Chapter 6, Liposome Technology, Vol. III, G. Gregoiaidis, ed., 1984. Generally, the ligands can be attached by a variety of linking groups to the amines in any phosphatidyl ethanolamine. T. D. Heath, et al., Biochim. Biophys. Acta, 599, 42–62 (1980) provides a particularly attractive way of attaching glycoproteins which is especially useful in immobilizing horseradish peroxidase and antibodies to the surface of a liposome.

The liposomes used in the present invention, for example, can be prepared by use of appropriately functionalized phospholipid reagents using generally known procedures for making liposomes as generally described in U.S. Pat. No. 4,913,902 to P. K. Kilpatrick et al. (see Col. 2, line 13 to Col. 4, line 6, for example) for the synthesis of liposomes carrying ligands adapted to bind to target molecules in solution for purification by affinity binding and ultimate filtration. The liposomes used for the present invention differ from the liposomes described in the aforementioned Kilpatrick et al. patent by the additional presence of a plurality of covalently bound labels, e.g., detectible markers, such as fluorophores, on the outer surface of the liposome body or catalysts (such as enzymes) for appropriate activation of an appropriate detectible marker adjacent the liposome.

The phospholipid structure can be appropriately modified at site A (A being $—(CH_2)_2NH—$ in the case of distearoylphosphatidyl ethanolamine with $m=16$ and A being $—(CH_2)_2NH_2$ with $m=14$ in the case of dipalmitoylphosphatidyl ethanolamine) in order to covalently link the desired label, e.g., detectible marker, such as a fluorophore, or enzyme:

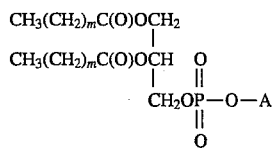

For example, in the case of the latter group A in the parenthetical given above, the linkage A can be of the formula: $—(CH_2)_2NHC(O)—F$, where F represents a fluorescein radical $C_{20}H_{11}O_5$ bonded thereto. Other coupling chemistries, known to persons of ordinary skill in the art can also be used to covalently couple other labels to the phospholipid molecule.

The liposomes used for the present invention provide for a significantly increased number of detectible markers or catalysts thereof and would thus provide for increased sensitivity. If a given liposome comprised a bilayer structure with 20,000 phospholipid molecules on the outer layer of the bilayer membrane and 13,000 phospholipid molecules on the inner layer, it would be comprised of a total of 33,000 molecules. If 5 to 20 percent of the total phospholipid content were fluorescent-conjugated, this would give 1,650 to 6,600 fluorescent groups per liposome attached to the bilayer structure. If four antibody or antigen groups were covalently attached to the liposome as well, the fluorescent group:ligand ratio would be from 412 to 1,650. This high ratio of fluorescent group to ligand provides a sensitive detection mechanism. In an analogous fashion the presence of a high ratio of enzyme groups, for example, can provide good sensitivity in ELISAs.

If an optical waveguide is used as the support for the immobilized antigen or antibody in an assay involving evanescent wave propagation in the bulk solution at the interface adjacent the support and the solution, liposomes of roughly 600Å to 700Å containing detectible fluorophore markers, for example, would be within the effective depth of penetration of the evanescent wave (about 1,000 to 2,000Å) depending upon the wavelength of the light.

The following Examples further illustrate the present invention.

MATERIALS FOR EXAMPLES 1–8

Materials

Affinity-purified polyclonal anti-biotin antibody (ABA), anti-goat, anti-mouse, anti-bovine IgG, cholesterol, distearoylphosphatidyl choline (DSPC), distearoylphosphatidyl ethanolamine (DSPE), dipalmitoylphosphatidyl ethanolamine (DPPE), DPPE covalently modified by attachment to fluorescein isothiocyanate (DPPE-FITC), and bovine serum albumin (BSA) were all purchased from Sigma Chemical Co., St. Louis, Mo. Flat sheets of polymethyl methacrylate (PMMA) were obtained from Goodfellow, Cambridge, England. Radioactive $C^{14}$-formaldehyde (10 mCi/mmol) was purchased from the Du Pont Co., Wilmington, Del., and $C^{14}$-biotin (53 mCi/mmol) was obtained from the Amersham Co., Arlington Heights, Ill. FITC-Biotin was purchased from Molecular Probes, Inc., Eugene, Org. Biotinyl-iminohexanoyl-N-hydroxysuccinimide ester, or long-chain biotin (biotin-LC-NHS) and the cleaning solvent RBS were both obtained from the Pierce Chemical Co. All solvents were reagent grade or better. The scintillation cocktail used was Scintiverse II, sold by the Fisher Scientific Co., Pittsburgh, Pa.

EXAMPLE 1

Biotinylated distearoylphosphatidyl ethanolamine (DSPE-Biotin) was prepared by the conjugation of LC-Biotin-NHS to DSPE according to the procedure of Bayer and Wilcheck in Liposome Technology, Vol. 3, pp. 127–135 (1984). DSPE (30 mg) was dissolved in 2 ml of chloroform:methanol (volume ratio of 9:1) containing 20 mg of biotin-LC-NHS and 120 μl of triethylamine. The reaction was carried out at room temperature for two hours. Biotinylated DSPE was separated from unreacted long-chain biotin and DSPE by preparative thin-layer chromatography on 1 mm-thick silica gel plates. The reaction mixture was loaded on silica plates in which the gel had been activated at 110° C. for fifteen minutes and was cooled to room temperature. The components were developed using a chloroform:methanol:water mixture (volume ratio of 80:25:2) for seventy minutes. The DSPE-Biotin was identified by both a biotin-specific spray agent (dimethylaminocinnamaldehyde, 0.2% in acidified ethanol, in McCormick and Roth, *Methods in Enzymology*, Vol. 18A, p. 383, 1970) and a phosphate-specific spray reagent (molybdenum blue reagent, Dittmer and Lester, J. Lipid Res., 5, 126–127, 1964). The DSPE-Biotin was scraped off the plate and extracted twice with 30 ml of chloroform:methanol (volume ratio of 9:1). The solvent was evaporated in a rotary evaporator at 48° C. and the product was stored in desiccated condition at −20° C. until used.

EXAMPLE 2

Small unilamellar vesicles were prepared using a procedure similar to that reported previously (Powers et al., Biotechnology & Bioengineering, Vol. 36, pp. 506–519, 1990). To make the vesicles used in the adsorption studies and in the competitive assays, cholesterol (8.67 mg), DSPC (17.7 mg), DPPE-FITC (1.31 mg) and DSPE-Biotin (2.37 mg) were dissolved in 5 ml of chloroform:methanol (volume ratio of 9:1). The solution was dried in a rotary evaporator at 60° C. for one hour, and the dried lipids were suspended in 15 ml of phosphate-buffered saline at pH 7.4 (from now on designated simply as PBS). The dispersion was sonicated for thirty minutes at 55° C. (Model W-385, Heat Systems Ultrasonics, Farmingdale, N.Y.) equipped with a titanium tip. After sonication, undispersed phospholipids were removed by filtration through a 0.2 µm Acrodisc filter (Gelman Sciences, Ann Arbor, Mich.), and the liposomes were stored at 4° C. Liposomes without biotin were prepared from cholesterol (9.42 mg), DSPC (19.24 mg) and DPPE-FITC (1.35 mg) in the same way. In the self-quenching experiments, the liposomes consisted of cholesterol, DMPC, DPPE-FITC and DMPE-Biotin. The molar concentration of DMPE-Biotin was fixed at 5%, and the molar concentration of cholesterol and DMPC were equal. The concentrations of cholesterol and DMPC were decreased as necessary as the molar concentration of DPPE-FITC was increased from 0.42% to 15%.

Average vesicle diameters were determined using light scattering as described previously (Powers et al., Biotechnology & Bioengineering, Vol. 33, pp. 173–182, 1989). Liposome samples were prepared by first photobleaching the FITC on the surface by prolonged exposure to laser light at 488 nm. The samples were then filtered through a 0.2 µm disposable Acrodisc filter to remove dust particles. The light scattering experiments were done using a Coherent Innova 70-3 argon laser (5 mW), set at 488 nm, and equipped with a Brookhaven model H goniometer and correlator. The intensity fluctuations of the scattered light at 90° to the incident beam were analyzed to determine an average diffusion coefficient for the liposomes. The average diameter of the vesicles was then calculated using the Stokes-Einstein equation.

If the FITC groups on DPPE-FITC are placed too close together on the surface of the vesicles, the fluorescent emission from one group could be absorbed by neighboring DPPE-FITC molecules. As a result, it was important to determine the optimal concentration of DPPE-FITC to be used in the membrane composition. Fluorescence measurements were carried out in a fluorescence spectrophotometer from SLM Instruments, Model 8000, Urbana, Ill., set at an excitation wavelength of 488 nm and an emission wavelength of 520 nm. Vesicle solutions of 2 mg/ml of phospholipid were prepared, with mole percents of DPPE-FITC in the vesicles of 0.42, 2.5, 5 and 15%. These solutions were diluted 2000-fold prior to each measurement.

PMMA cuvettes were cleaned by sonication for twelve hours in RBS solution, followed by sonication in deionized water for twenty-four hours. The cuvettes were incubated in 0.2 ml of 40 µg/ml of anti-biotin antibody (ABA) solution in PBS for two hours at room temperature and rinsed with 0.4 ml PBS twice to remove unbound antibody. The cuvettes were then incubated in 0.2 ml of 3 weight % BSA solution in PBS as a blocking agent for one hour at room temperature, and rinsed twice with 0.4 ml of PBS. Other antibodies were adsorbed to the cuvettes to test for specificity of the interaction by using exactly the same procedures, simply replacing ABA by the appropriate antibody: anti-goat, anti-mouse or anti-bovine IgG. PMMA plates (approximately 1.5 cm×1.5 cm) used in the antibody adsorption studies were cleaned in the same way as the PMMA cuvettes. To adsorb antibody to the PMMA plates, four of the plates were incubated in 10 ml of a 40 µg/ml solution of ABA in PBS for two hours at room temperature and rinsed twice with 10 ml of PBS. The plates were then incubated in 10 ml of 3% weight BSA solution in PBS for one hour at room temperature, and rinsed twice with 10 ml of PBS.

The total amount of ABA adsorbed per unit area of PMMA was determined by radiolabeling the antibody, and measuring the amount of radioactivity adsorbed to PMMA plates in a scintillation counter. $C^{14}$-labeled anti-biotin was prepared by reductive methylation with $C^{14}$-formaldehyde. Then, 50 µl of a 0.1M NaCNBH$_3$ solution was added to 1 of a 2 mg/ml ABA solution in PBS. After mixing, 1 µCi of $C^{14}$-formaldehyde was allowed to react for two hours at room temperature. The reaction mixture was dialyzed at 4° C. extensively against five changes of 1 liter PBS in order to remove unreacted formaldehyde and formaldehyde in labile adducts with other functional groups on the protein (Jentoft and Dearborn, Methods in Enzymology, Vol. 91, pp. 570–579, 1983). The resulting specific activity of the radiolabeled anti-biotin, determined by scintillation counting (Hewlett Packard Co., Model 1500, Palo Alto, Calif.) was $4.4 \times 10^5$ DPM/mg of protein, which corresponds to approximately 0.3 $C^{14}$-methyl groups per protein molecule. Removal of the PMMA slides from the scintillation counter had no effect on the counts per minute, indicating that the protein was desorbed from the polymer upon contacting the organic scintillation cocktail.

EXAMPLE 3

The adsorption of biotin to the antibody-coated PMMA surface was studied by exposing the surfaces to $C^{14}$-labeled biotin, washing the slides, and determining the amount of radioactivity remaining on the solid support at different initial concentrations of biotin in the bulk solution. Four PMMA slides (1.5 cm×1.5 cm) coated with antibody, as described above, were incubated in 10 ml of $C^{14}$-biotin PBS solutions in the concentration range from $10^{-8}$ to $10^{-4}$M. After a ninety minute exposure, the slides were dipped quickly in 200 ml of deionized water to remove unbound $C^{14}$-biotin from the surface. The radioactivity of the slides was determined by scintillation counting. Removal of the slides from the scintillation counter did not affect the counts per minute, indicating that the protein and biotin were both desorbed from the PMMA slides upon exposure to the scintillation cocktail. As a control, the non-specific adsorption of $C^{14}$-biotin to PMMA alone and to BSA-covered PMMA was tested the same way, using a $C^{14}$-biotin concentration of $10^{-4}$M.

Figure 2A:
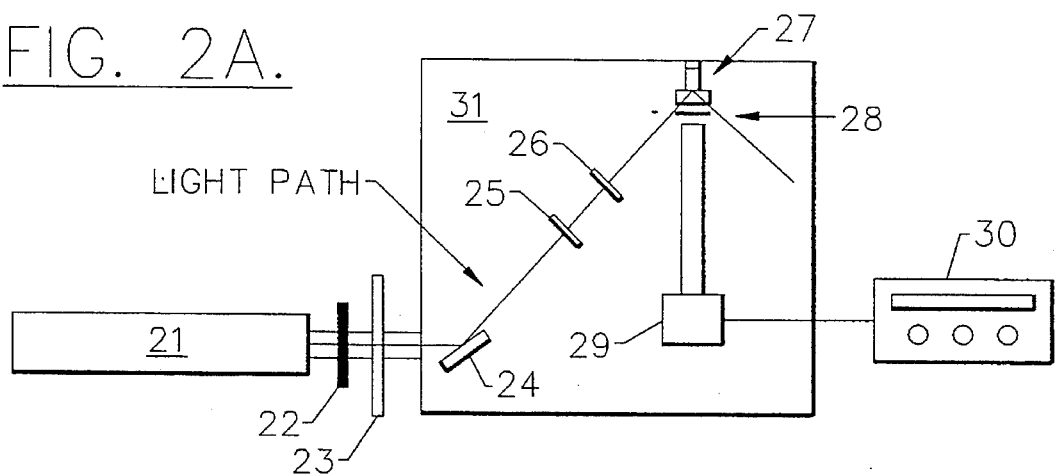
FIG. 2A is a schematic view of the apparatus for total internal reflection fluorescence (TIRF) in accordance with an embodiment of the invention.
Figure 2B:
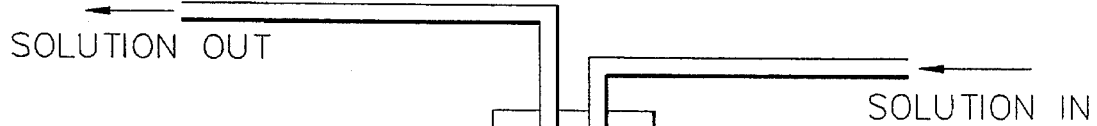
FIG. 2B is a schematic view of the flow-through sample cell used in the apparatus of FIG. 3A showing the critical angle for total internal reflection at the cuvette-water interface.
Figure 2B:
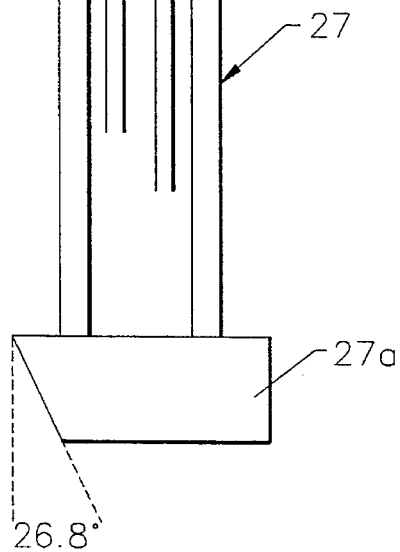

A schematic diagram of the basic equipment used for the TIRF measurements using the fluorescent liposomes and the FITC-Biotin is shown in FIGS. 2A and 2B (schematic of flowthrough cuvette) A 10-mW argon ion laser 21 (Model 161C, Spectra-Physics, Mountain View, Calif.) tuned to the 488 nm line was used as the light source since it closely matched the 493 nm absorption maximum of fluorescein. A manual shutter 22 was attached to the laser so that essentially no light would reach the sample when the shutter was closed. The shutter was open for only a few seconds during a given measurement. The laser beam passed through a rotating beam chopper 23 (Model 75155, Oriel Co., Stratford, Conn.) used to help minimize the photobleaching of fluorescein during exposure to the light source. An elliptical mirror 24 (Edmund Scientific Co., Barrington, N.J.) was used to deflect the light at the critical angle (63.2°) for the PMMA cuvette 27, best seen in FIG. 2B. A 488 nm filter 25 and a variable iris were placed in the reflected beam to reduce the amount of stray light from other sources hitting the cuvette 27. The shape of the cuvette 27 is best shown in FIG. 2B. It was made completely out of PMMA. It was designed so that there would be only a single internal reflection from the PMMA-solution interface, and so that it would have a flow-through capability to allow the solution to be changed without removing the cuvette 27 from the holder. The total volume of the cuvette was 0.53 ml. At the polymer-solution interface an evanescent wave originated, and it excited any fluorescent molecules within approximately less than 1000 Å from the interface. The emitted fluorescence was detected by a photomultiplier tube 29 (Hamamatsu Co., Hamamatsu, Japan). A 520 nm filter 28 was placed on top of the tube so that only the emitted light from fluorescein would be measured. The output from the photomultiplier 29 was sent to a preamplifier, not shown, (Model C716, Hamamatsu) and recorded using a digital photon counter 30 (Model C1230, Hamamatsu). The mirror, the filters, the iris, the cuvette and the photomultiplier tube were all contained in a black enclosure 31 to eliminate stray light.

The adsorption of fluorescent biotin-conjugated liposomes and FITC-Biotin to the surface of the PMMA cuvettes was studied by measuring the amount of fluorescence remaining on the surface of the cuvette after exposure to a known concentration of fluorescent species and a washing step with PBS. One milliliter of solution containing fluorescent species was injected into the inlet of the cuvette 27 with a syringe, and the solution was allowed to stand in the cuvette for either half an hour or an hour, depending on the experiment. Unbound fluorescent molecules were then washed from the cuvette by pumping PBS with a peristaltic pump at a flow rate of 1 /min. After washing, the shutter 22 on the laser 21 was opened for a few seconds, until the digital reading on the photomultiplier tube counter 30 stabilized. This was recorded as the fluorescent signal in kilo-counts per second (KCPS) coming from the interface. In some cases, measurements were taken at short intervals of time (0.5 minutes) and the washing continued. This was done when it was necessary to investigate the role of the washing step in reducing the measured fluorescence signal. In other cases, the washing time was extended past ten minutes to see if it was possible to remove vesicles or FITC-Biotin from the surface by extensive washing with PBS. Most of the liposome adsorption values reported were taken after a ten minute washing step. This incubation and washing procedure was followed regardless of the type of fluorescent species (liposomes or FITC-Biotin), or the concentration of the species in solution. Liposome concentrations in the range from $10^{-3}$ mg/ml to 1.0 mg/ml of phospholipid, and FITC-Biotin concentrations from $10^{-7}$ to $10^{-4}$M were tested. During competitive assay studies between liposomes and free biotin, the injected sample contained the desired concentration of vesicles and biotin in PBS, and the washing solution was PBS. In some instances, a solution containing biotin at the same concentration as the injected sample was used to wash the liposome-covered surface to see if the biotin could replace bound liposomes at the interface.

To check the specificity of the interaction between the liposomes and the surface, two different kinds of experiments were carried out. Fluorescent vesicles were made without biotin on the surface, and the adsorption to PMMA covered with ABA was detected. In addition, ABA was replaced in several experiments by avidin, anti-goat, anti-mouse and anti-bovine polyclonal IgGs. The adsorption of fluorescent vesicles with and without biotin on these surfaces was also recorded.

RESULTS AND DISCUSSION

Surface Characterization

Using radiolabeled ABA, it was determined that PE was able to adsorb approximately 360 ng of antibody/$cm^2$ in PBS at pH 7.4. Based on a molecular weight for the antibody of 150,000 Daltons, this corresponds to an area per molecule of approximately 83 Å×83 Å, which is similar to that of a closed-packed configuration. The value of 360 ng/$cm^2$ is in the range of previously reported values for antibody surface adsorption to polymers (Harlowe and Lane, Immunoassays, in Antibodies, Cold Spring Harbor Laboratory, N.Y., 1988, pp. 553–612). The equivalent total number of moles of antibody per unit area of PMMA obtained was $2.4 \times 10^{-12}$ moles/$cm^2$.

Figure 3:
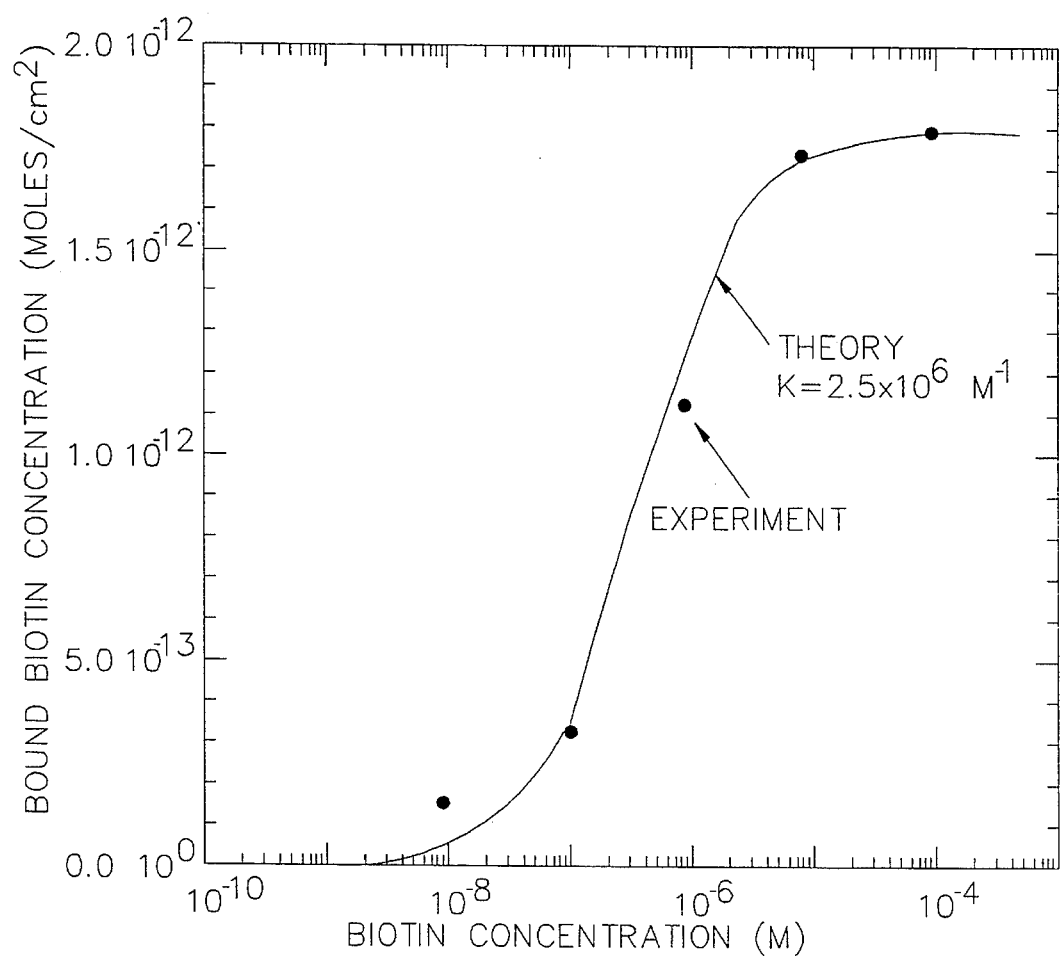
FIG. 3 shows a plot of the binding isotherm for free biotin to polymethylmethacrylate coated with anti-biotin antibody and blocked with bovine serum albumen (BSA) in accordance with one embodiment of the invention. The theory line was obtained from the Langmuir isotherm with $K=2.5 \times 10^6 \text{ M}^{-1}$.

The ability of the antibody-covered surface to bind biotin based on the results of radioimmunoassays is indicated by the isotherm shown in FIG. 3. The number of moles of biotin bound per unit area of surface is shown as a function of the initial concentration of biotin to which the surface was exposed. For concentrations of biotin greater than $10^{-4}$M, the surface becomes saturated with biotin at a level of approximately $1.8 \times 10^{-12}$ moles of biotin/$cm^2$. Assuming that each antibody molecule adsorbed to the surface can bind two biotin molecules, this corresponds to $0.88 \times 10^{-12}$ moles of active ABA/$cm^2$. Based on an initial value of $2.4 \times 10^{-12}$ moles/$cm^2$ of total antibiotin bound, approximately 37% of the adsorbed antibody molecules are effective in binding biotin.

An analysis of the data in FIG. 3 can lead to an estimate the strength of the binding constant between biotin and the adsorbed ABA. The interaction between ligand in solution (free biotin initially) and the antibody on the surface can be analyzed considering a single equilibrium binding step $$Ab_{(s)} + L \rightleftharpoons AbL_{(s)} \tag{1}$$

where $AbL_{(s)}$ represents an antibody-biotin complex on the solid surface. The equilibrium constant can be written in the form $$K = \frac{\Gamma_{AbL}}{\Gamma_{Ab}[L]} \quad (2)$$

Here the quantities Γ represent the surface concentrations of the free antibody binding sites (Ab) and the biotin-bound antibody binding sites (AbL) in moles/cm². The biotin can be found either free in solution, or bound to the surface, so that a biotin balance in the system gives rise to the equation $$[L_o]=[L]+\Gamma_{AbL} A_V \quad (3)$$

where $[L_o]$ is the initial ligand concentration in bulk solution, A is the total area of solid available for binding during an experiment (four slides for a total area of 18.8 cm²) and V is the solution volume (10 ml). Similarly, an antibody balance gives rise to the equation $$\Gamma_{Ab}0 = \Gamma_{Ab} + \Gamma_{AbL} \quad (4)$$

in which $\Gamma_{Ab}0$ is the initial concentration of antibody binding sites, namely, $1.8 \times 10^{-12}$ moles/cm². Substituting equations 3 and 4 into equation 1 results in an equation for the surface concentration of bound biotin (ΓAbL) where the only unknown is K, the equilibrium binding constant on the surface, $$K([L_o]-a_v\Gamma_{AbL})(\Gamma_{Ab\ o}-\Gamma_{AbL})=\Gamma_{AbL}. \quad (5)$$

The quantity $a_v$ is the ratio (A/V) which equals 1.88 cm⁻¹ in these experiments. The amount of bound biotin $a_v\Gamma_{AbL}$ is always much less than the initial $[L_o]$, so that to a good approximation, equation 5 reduces to $$\Gamma_{AbL} = \Gamma_{Ab^o} \frac{K[L_o]}{1+K[L_o]} \quad (6)$$

Equation 6 is the equation for a Langmuir adsorption isotherm, written in terms of the initial ligand concentration present in the sample. A best fit of the value of K to the experimental data resulted in a value of $2.5 \times 10^6$ M⁻¹, and the result of equation 6 using this value of K is shown in FIG. 3. This value of K is of the same order of magnitude as the equilibrium binding constant of this antibody for biotin in bulk solution.

EXAMPLE 4

The vesicles used in this study contained DSPC and cholesterol as the main structural components. Cholesterol is known to stabilize phospholipid vesicles that are subjected to temperature changes and to the presence of high protein concentrations in solution (Kirby et al., Biochem. J., Vol. 186, pp. 591–598, 1980). Cholesterol-containing vesicles have also been used in the few previous studies where liposomes have been bound by specific interactions to solid surfaces (O'Connell et al., Clin. Chem., 31(9), 1424–1426, 1985; and Campbell et al., U.S. Pat. No. 4,743,560, 1988), with no apparent disruption upon adsorption. It was deemed that the use of approximately 40 mole % cholesterol in these investigations would prevent disruption of the liposome structure upon binding to PMMA, a predominantly hydrophobic polymeric support, once it had been modified by adsorption of antibody and BSA.

Vesicles with concentrations of DPPE-FITC from 0.42 to 15 mole % were synthesized, but because of the self-quenching properties of fluorescein, it was found that there was an optimal concentration that should be used in order to enhance the signal. Vesicles containing the same amount of cholesterol and DSPC, but varying amounts of DPPE-FITC (0.42, 2.5, 5 and 15 mole %), were prepared and the fluorescence of the solution measured. If there were no self-quenching, the fluorescence at 520 nm due to excitation at 488 nm from two vesicle solutions with two different percentages of DPPE-FITC should be proportional to the percent DPPE-FITC. However, when there is self-quenching, the measured fluorescence for larger percentages of fluorescein will not be proportional to this percentage.

The values for the number of fluors per vesicle (N) for the different DPPE-FITC concentrations used can be estimated based on an average vesicle diameter of 570 Å, the value determined from quasi-elastic light scattering as described in this experimental section. From the results of Israelachvilli and Mitchell, Biochim., Biophys. Acta, Vol. 389, pp. 13–19 (1975) and Johnson, Biochim. Biophys. Acta, 307, 27–41 (1973), the cross sectional areas of single phosphatidyl choline and cholesterol molecules in a vesicle bilayer are 71 Å² and 38 Å² respectively. Since substantially all the vesicles comprised mostly DPPC and cholesterol in equal concentrations, the average area per lipid in the vesicles was approximately 54.5 Å². Considering that approximately 60% of the phospholipid molecules in small unilamellar vesicles are on this outside layer (Powers et al., Biotechnology & Bioengineering 36, 506–519, 1990), this leads to approximately 31,200 lipid molecules per liposome of this average size.

TABLE 1

Estimate of the total number of fluorescent groups per vesicle at different concentrations of DPPE-FITC (10⁻³ mg/ml phospholipid vesicle solutions).

| DPPE-FITC (Mole %) | Fluors/ vesicle (N) | Signal (counts/s) | Signal/ fluor (F) | % Quenching |
|---|---|---|---|---|
| 0.42 | 131 | 7,476 | 57 | — |
| 2.5 | 780 | 34,083 | 44 | 23 |
| 5.0 | 1,560 | 43,888 | 28 | 51 |
| 15.0 | 4,680 | 49,973 | 11 | 81 |

The signal/fluor values (F) in Table 1, above, are obtained by dividing the signal values by the number of fluors/vesicle (N). It is apparent that the higher the percentage of fluorescein in the vesicles, the lower the efficiency of fluorescence. This can be seen a little better if the value of F at the higher DPPE-FITC percentages is divided by the value of F at 0.42 mole % (F=57) where self-quenching is at a minimum. The results are shown as % Quenching in Table 1, where the % Quenching is calculated by the formula % Quenching=[1−F/57]×100

Clearly, once a value of 2.5 mole % DPPE-FITC is exceeded, more than half the fluorescence is quenched. As a result, the value of 2.5 mole % was chosen for the concentration of the fluorescent groups for all subsequent experiments.

Once the fluorescein concentration on the liposomes is fixed at 2.5 mole % by this procedure, an approximate area/fluorescein molecule can be estimated. Of the 780 DPPE-FITC molecules per vesicle, 60% or 470 are on the outside layer, which has an area of $1 \times 10^6$ Å² for a 570 Å-diameter vesicle. This gives an area per DPPE-FITC molecule of approximately 2,127 Å², or 46 Å×46 Å per molecule. The 46 Å average distance of separation is apparently sufficient to significantly decrease the self-quenching of fluorescein.

The DSPE-Biotin concentration on the liposomes was chosen to be 5 mole %. This corresponds to approximately 1560 biotin molecules per vesicle, of which approximately 936 are on the outside layer. This gives an area per biotin molecule of 1,068 Å$^2$, or approximately one biotin molecule every 33 Å×33 Å. These estimations indicate that the distances between biotin molecules on the vesicle surface are much closer than the distances between antibodies on PMMA. This provides ample opportunity for the biotin to bind to the support, and it allows the possibility of multiple binding of the vesicle to the solid. Since the fluorescein concentration on the vesicle walls is almost as large as that of the hapten (biotin), unless the hapten is sufficiently removed from the liposome surface, it is likely that its binding to antibody will be affected by the presence of the fluorescent moieties.

The distance of separation between the end of the double ring of biotin and the phospholipid head group in DSPE-Biotin is approximately 22 Å, largely provided by the length of the spacer in long-chain biotin. The distance of separation of the three-ring portion of FITC from the phospholipid is roughly 13 Å. As will be shown in the next Example, this extra spacing serves to make the biotin accessible to binding of both anti-biotin antibody and avidin adsorbed on the solid support, even though the FITC molecule is larger than biotin. The fact that biotin is more accessible serves to control the interaction of the modified vesicles with the protein-coated surface.

EXAMPLE 5

Figure 4:
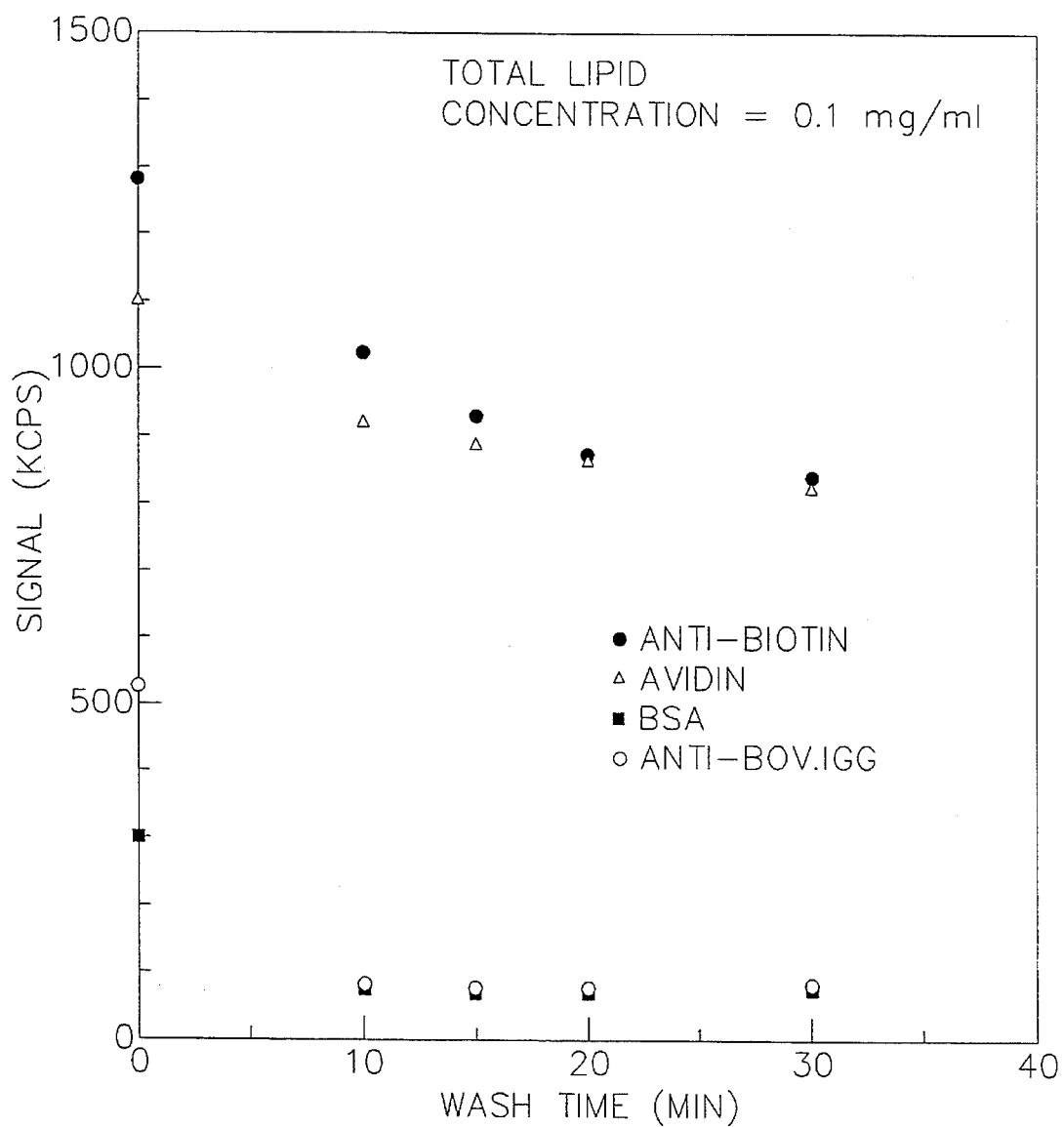
FIG. 4 is a plot of the fluorescence signal coming from the surface of protein-covered polymethylmethacrylate (PMMA) sample cells exposed to fluorescent biotinylated vesicles during the wash step with PBS.

Solutions containing fluorescent biotin-conjugated vesicles in PBS at a total lipid concentration of 0.1 mg/ml (phospholips plus cholesterol) were introduced into the sample cuvettes in the TIRF apparatus, and allowed to stand for a period of one hour. After this time, fresh PBS solution was introduced into the cuvettes, and the fluorescence remaining on the surface was measured as a function of time during this wash cycle. Sample results are shown in FIG. 4, for cuvettes that had been coated with anti-biotin antibody (ABA), avidin, BSA and an anti-bovine IgG with no particular specificity for biotin. The signals obtained when the surface was modified by ABA and avidin are much greater than the signals obtained when only BSA or the anti-bovine IgG were present on the surface. This is indicative of the specificity of the interaction of the biotinylated vesicles with ABA and avidin on the surface. The volumetric flow rate used during the washing step was 1 ml/min, and given the cuvette volume of 0.53 ml, the residence time for the liquid in the cuvette was approximately 0.5 minute. The decrease in fluorescence signal shown in FIG. 4, from time zero to ten minutes, was partly due to the washing of the bulk solution from the cuvette, and perhaps to some small amount of desorption of vesicles from the surface. After the ten-minute period, most of the fluorescence drop is due to the bleaching of fluorescein by the repeated exposure to laser light every few minutes. This slight drop in fluorescence was seen even when fluid was not being pumped through the sample cell.

Table No. 2 compares the fluorescence remaining after a ten-minute wash on surfaces coated with ABA, BSA, and three different types of antibodies not specific to biotin. In all of these experiments, the total lipid concentration was maintained constant at 0.1 mg/ml:

TABLE 2

| FITC-Vesicles with 5 mole % Biotin | |
|---|---|
| Surface | Signal After Washing (KCPS) |
| Anti-Biotin Antibody | 910 |
| Avidin | 875 |
| Non-Specific Goat IgG | 150 |
| Non-Specific Mouse IgG | 115 |
| Non-Specific Bovine IgG | 75 |
| BSA | 50 |

The signals obtained with ABA and avidin are at least a factor of eight greater than those obtained due to the non-specific binding of vesicles to BSA and the other antibodies. This is good evidence that the interactions of the biotinylated vesicles with the ABA-coated PMMA, after blocking with BSA, showed a high degree of specificity.

On the other hand, if the biotin is not included in the liposome formulation, the presence of fluorescein on the surface of the vesicles induces a large degree of non-specific binding. This can be seen in Table No. 3:

TABLE 3

| Surface | Signal After Washing (KCPS) |
|---|---|
| Anti-Biotin Antibody | 495 |
| Avidin | 660 |
| Non-Specific Goat IgG | 280 |
| Non-Specific Mouse IgG | 120 |
| Non-Specific Bovine IgG | 305 |
| BSA | 300 |

The signals obtained when the vesicles without biotin adsorb to avidin and to ABA on the PMMA are significantly lower than those obtained when biotin is present on the liposomes. On the other hand, the fluorescence signal with BSA and other IgG's on the surface is much greater when the biotin is not present, than when it is present on the vesicles. This is indicative of non-specific binding of the fluorescein to the proteins adsorbed on the solid. It is not surprising to find this type of non-specific binding, since the structure of fluorescein is similar in many ways to that of dyes which are often used in dye-ligand chromatography. However, the presence of biotin in larger concentration on the surface (5 mole %, as opposed to 2.5 mole % fluorescein) changes the surface properties completely. It reduces non-specific binding dramatically, as indicated by the comparison between the results in Table Nos. 2 and 3. It is interesting to note that without biotin, fluorescein binds a little more strongly to avidin and to anti-biotin antibody than it does to BSA and the other IgG's on the surface. It is apparent that both avidin and anti-biotin antibody have a higher affinity for fluorescein than to the other proteins adsorbed to the PMMA.

The fluorescence signal coming from the surface should be related to the number of vesicles per unit area adsorbed to the solid. If the interaction of the vesicles with the antibody on the surface is an equilibrium process, described mathematically by an association step as shown in equation 1, it should be possible to measure an adsorption isotherm which is time-independent. Sample cuvettes were exposed to PBS solutions containing various concentrations of liposomes. The fluorescence signal was recorded after a ten-minute wash with PBS, with times of exposure of either one hour or one-half hour. The concentration of vesicles in moles/liter was determined from a knowledge of the phospholipid concentration in mg/ml, and an estimate of the molecular weight of vesicles with a diameter determined from quasi-elastic light scattering (570 Å). As discussed previously, such vesicles should contain approximately 31,200 lipid molecules. Using the molecular weight and the composition of each of the components (cholesterol, DSPC, DPPE-FITC and DSPE-Biotin), the average molecular weight of a lipid molecule in the vesicles is 623. This gives an approximate molecular weight for the entire vesicle of $19.4 \times 10^6$ daltons. A lipid concentration of 1 mg/ml corresponds to a $5.15 \times 10^{-8}$M concentration of vesicles. As expected, the larger the concentration of liposomes in bulk solution, the larger the fluorescence signal coming from the surface. It was also found that the measured signal was the same with either one hour or one-half hour of exposure of the vesicle solution to the antibody-coated surface. Because of the flow-through nature of the cuvette being used in these experiments, there is a significant amount of fluid motion during the introduction of samples to the cell. This convective transport may be reducing the amount of time required to equilibrate the surface with the bulk solution. The resulting data can then be properly interpreted as an equilibrium isotherm. This assumes that the desorption step of vesicles from the surface is a much-slower step than adsorption, so that little fluorescence is lost during the wash step. That this is indeed the case is evident from the results shown in FIG. 4.

EXAMPLE 6

The binding isotherm data may be analyzed using a simple Langmuir adsorption model, as described by equation 6. The ratio of adsorbed liposomes to the maximum number that can be adsorbed can be interpreted as the ratio of the signal measured at a given liposome concentration to the maximum signal obtained $$\lambda = \frac{\Gamma_{AbL}}{\Gamma_{max}} = \frac{\text{SIGNAL}}{\text{MAX.SIGNAL}} = \frac{K_L[L_o]}{1 + K_L[L_o]} \qquad (7)$$

Here, $\Gamma_{max}$ refers to maximum number of moles of liposome/cm$^2$ of surface which can be adsorbed to the solid, and $\Gamma_{AbL}$ is the surface liposome concentration (moles/cm$^2$) adsorbed at a given bulk liposome concentration $[L_o]$. As with the adsorption isotherm measurements done with free biotin and analyzed in FIG. 3, the free liposome concentration in bulk solution after equilibration is approximately equal to the initial concentration. MAX. SIGNAL is the value of the fluorescence signal at a liposome concentration of $5 \times 10^{-8}$M, approximately 1250 KCPS, and SIGNAL is the fluorescence signal measured at any lower liposome concentration.

Figure 5:
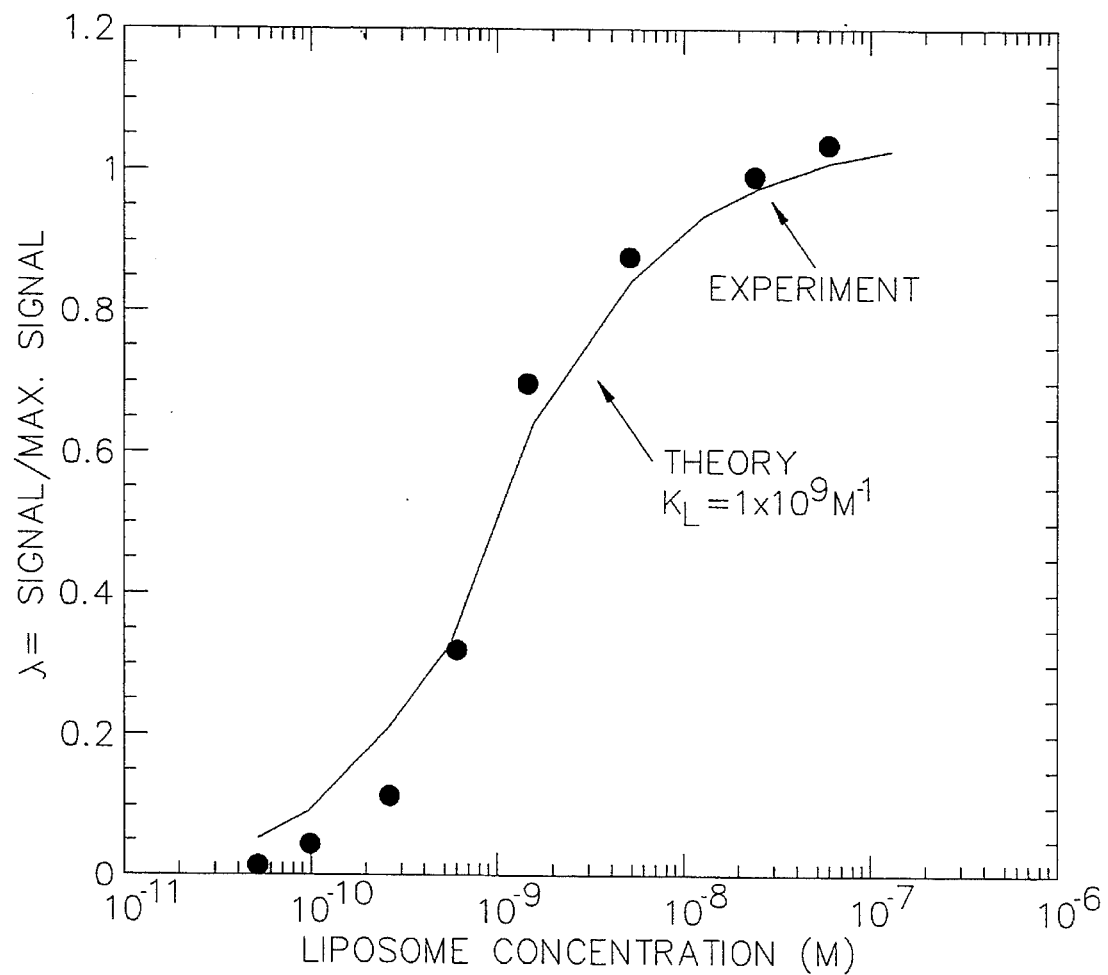
FIG. 5 is an estimate of the binding constant for biotinylated vesicles to PMMA coated with anti-biotin antibody and blocked with BSA. (Theory line obtained from Langmuir isotherm, with $K_L=1 \times 10^9 \text{ M}^{-1}$)

The experimental data can be analyzed using equation 7 to calculate an approximate adsorption equilibrium constant $K_L$ for the liposomes on the antibody-coated PMMA. The results are shown in FIG. 5. The adsorption equilibrium constant for the fluorescent biotinylated vesicles was found to be approximately $1 \times 10^9$M$^{-1}$. This is to be compared to the adsorption equilibrium constant of $2.5 \times 10^6$M$^{-1}$ measured for free biotin. It is apparent that the vesicles bind much more strongly to the surface than the free-biotin. This is possibly due to the binding of several biotin molecules on the liposome to antibody sites on the surface. As discussed earlier, the antibodies on the solid surface are spaced about 100 Å from each other, and the separation between biotin molecules on the surface of the vesicles is on the order of 33 Å. Since the vesicles have a diameter of 570 Å, there are ample opportunities for several biotin molecules on a given vesicle to bind to the solid.

Figure 6:
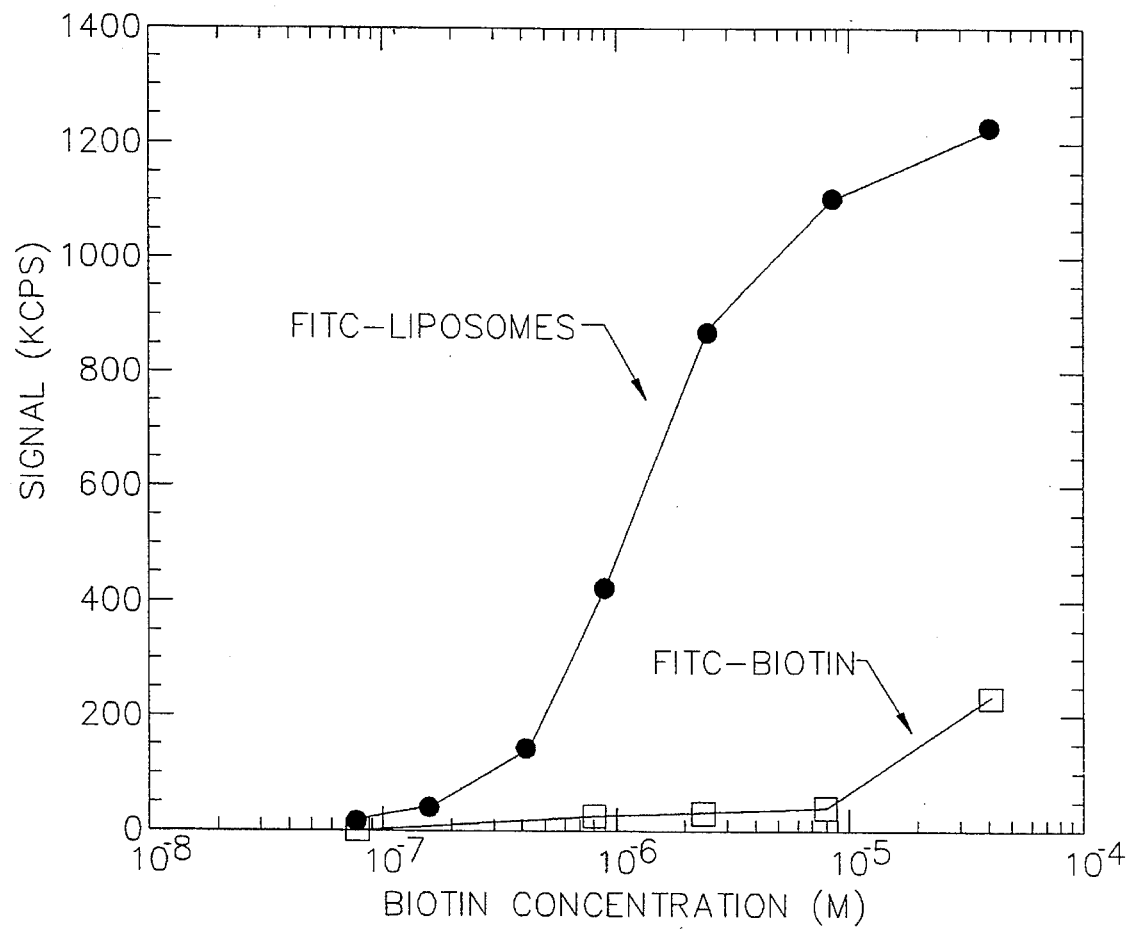
FIG. 6 provides a comparison of the fluorescence signal remaining after a ten minute wash of the sample cell with fluorescent biotinylated vesicles and fluorescein isothiocyanate-biotin (FITC-Biotin)
Figure 7:
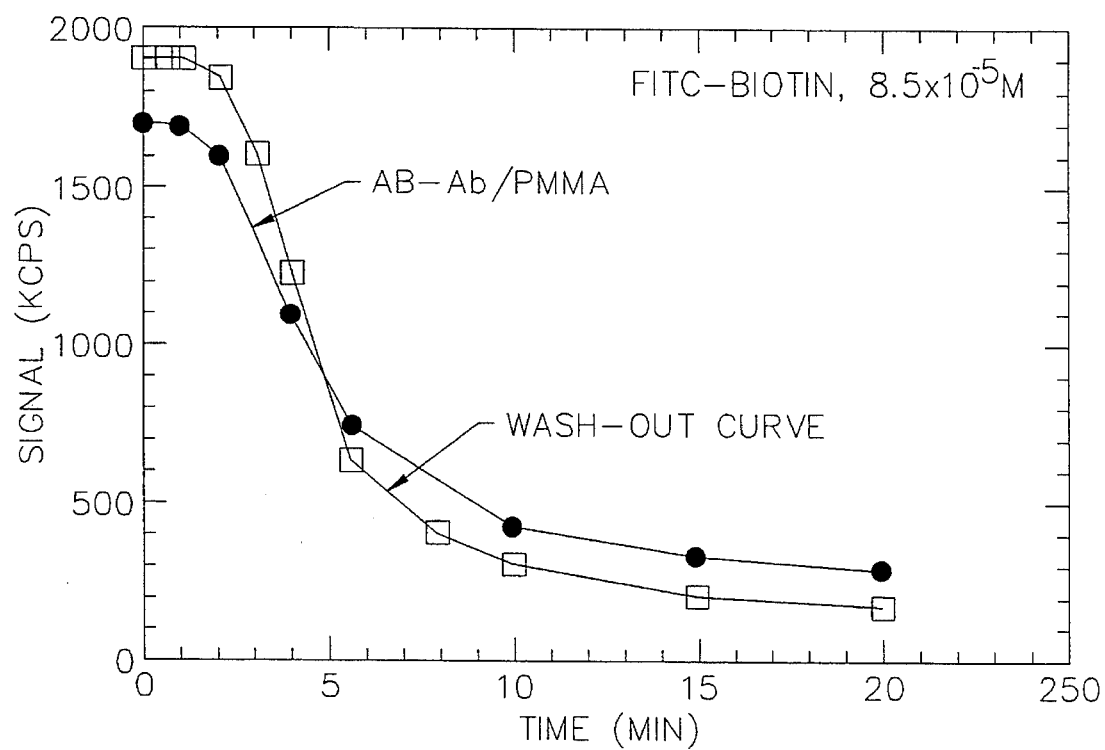
FIG. 7 shows the desorption of FITC-Biotin from the surface of the sample cell during the wash step.

It is of interest to compare the adsorption of the fluorescent biotinylated vesicles to the adsorption of FITC-Biotin on the same antibody-coated PMMA surface. FITC-Biotin solutions in PBS, in the concentration range of $10^{-8}$ to $10^{-4}$M, were exposed for one-half hour to the antibody-coated PMMA cuvettes. The cells were then washed for a period of ten minutes with PBS, and the fluorescence of the surface was recorded. The results are shown in FIG. 6, together with the fluorescence measurements obtained with liposomes at the same biotin molarity as FITC-Biotin. The biotin molarity of the vesicles was calculated by taking the liposome solution concentration in moles/liter (see FIG. 5) and multiplying by the number of biotin molecules per liposome (1560). Thus, the biotin concentrations are approximately three orders of magnitude larger than the vesicle concentrations. Obviously, there is a significant increase in signal when the vesicles are used. The main reason for this is that the adsorption equilibrium constant of FITC-Biotin on the surface is so low, that most of the FITC-Biotin molecules desorb during the washing step. This is illustrated in FIG. 7, which shows the decrease in fluorescence during a wash step where the initial FITC-Biotin concentration was $8 \times 10^{-5}$M, from a cuvette that with adsorbed anti-biotin antibody. The rate of decay of fluorescence in both cuvettes is essentially the same. It is apparent that the there is a very low association constant for FITC-Biotin to ABA. It was demonstrated earlier that pure biotin has an association constant of $2.5 \times 10^6$M$^{-1}$. The modification of biotin by the attachment of FITC evidently causes a significant reduction in the association constant, resulting in extremely low fluorescence signals. This is further evidence that the strong binding of the liposomes to the surface is probably caused by the attachment of several biotin molecules to the antibodies on the solid.

EXAMPLE 7

In order to study the competition between fluorescent biotinylated vesicles and free biotin in solution for binding sites on the antibody-coated surface, experiments were carried out where the liposome concentration was held constant, at either 0.01 mg/ml or 0.03 mg/ml and the free biotin concentration in solution was varied from $5 \times 10^{10}$M to $3 \times 10^{-3}$M. At 0.01 mg/ml of lipid, the molar concentration of liposomes is $5.15 \times 10^{-10}$M, and at 0.03 mg/ml it is $1.55 \times 10^{-9}$M. Given values of the adsorption equilibrium constant for free biotin ($K_B = 2.5 \times 10^6$M$^{-1}$), and for biotinylated liposomes ($K_L = 1 \times 10^9$M$^{-1}$), it is possible to make a prediction of the fraction of the surface covered by liposomes, and the fraction of the surface covered by biotin, using a simple Langmuir model for competitive adsorption $$\lambda_B = \frac{K_B[B_o]}{1 + K_B[B_o] + K_L[L_o]} \qquad (8)$$

$$\lambda_L = \frac{K_L[L_o]}{1 + K_B[B_o] + K_L[L_o]} \qquad (9)$$

The quantities $[L_o]$ and $[B_o]$ are the initial molar concentrations of liposomes and free biotin, respectively. Since the free biotin was not fluorescently-labeled, the only fluorescence measured is due to adsorbed fluorescent liposomes. The maximum signal obtained for adsorbed vesicles, at very high molar concentrations of liposomes, is approximately 1250 KCPS. The quantity $\lambda_L$ is estimated by taking the measured fluorescence at a given set of concentrations, and dividing by the maximum signal value for full surface coverage.

Figure 8:
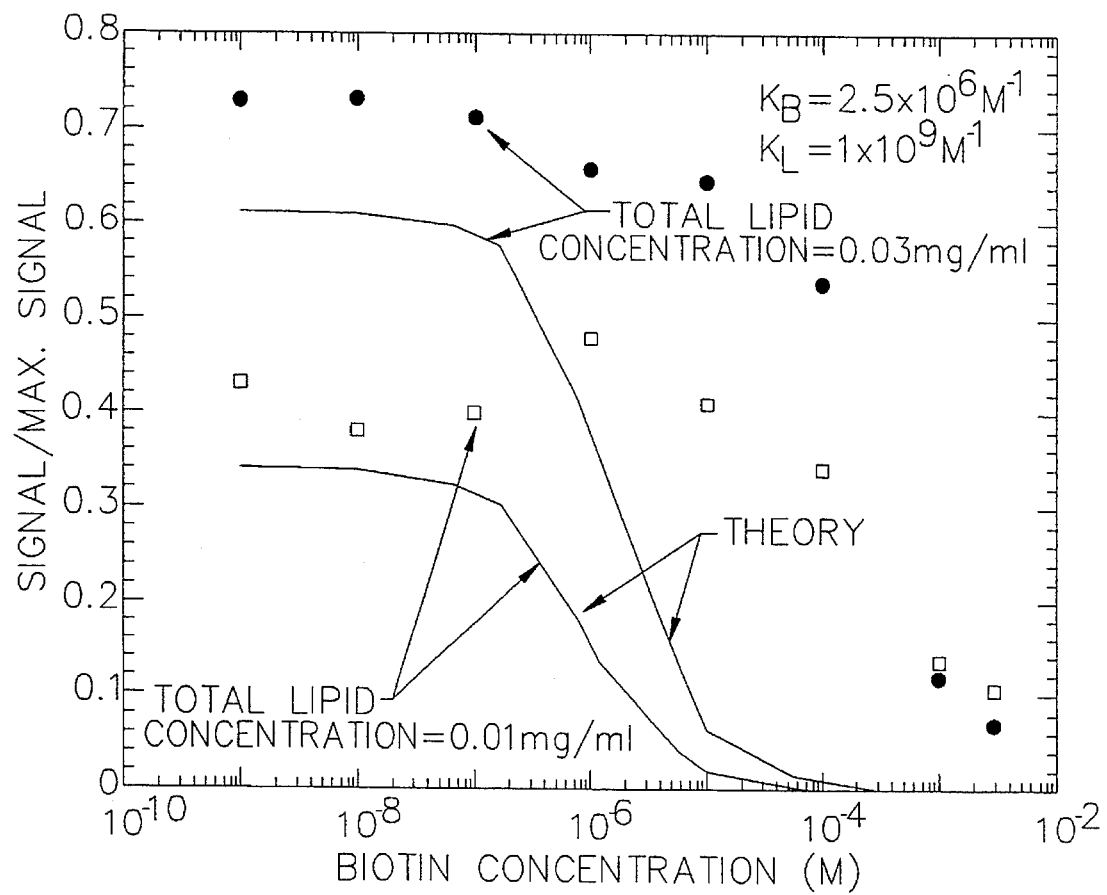
FIG. 8 shows the fluorescence signal as a function of free biotin concentration at two different constant values of liposome concentration. (Theory lines refer to a competitive Langmuir model with $K_B=2.5 \times 10^6 \text{ M}^{-1}$ and $K_L=1 \times 10^9 \text{ M}^{-1}$).

The results of these competition experiments is shown in FIG. 8, together with the predictions for $\lambda_L$ based on equation 9. At very low values of free biotin concentration ($10^{-10}$M), the signal approaches the values at $5\times10^{-10}$M and $1.55\times10^{-9}$M vesicle concentrations. As the free biotin concentration increases, the magnitude of the fluorescence decreases, indicating a reduced surface concentration of vesicles adsorbed to the solid. At high values of the free biotin concentration ($10^{-2}$M), the fluorescence from the surface decreases to nominal background values. The presence of large amounts of free biotin apparently reduces the ability of the vesicles to bind to the solid, in accordance with the way normal competitive solid-phase assays for free antigen are conducted. However, as can be seen from the theoretical results, the simple Langmuir model predicts that the fluorescence should decrease significantly beginning at a free biotin concentration of approximately $4\times10^{-7}$M, which roughly corresponds to the inverse of the association constant. The experimental results show that the decrease in fluorescence does not commence until the free biotin concentration is approximately $2\times10^{-5}$M.

EXAMPLE 8

This Example illustrates a sandwich assay procedure using the fluorescent liposomes whose synthesis was earlier described in Examples 1–2.

Figure 9:
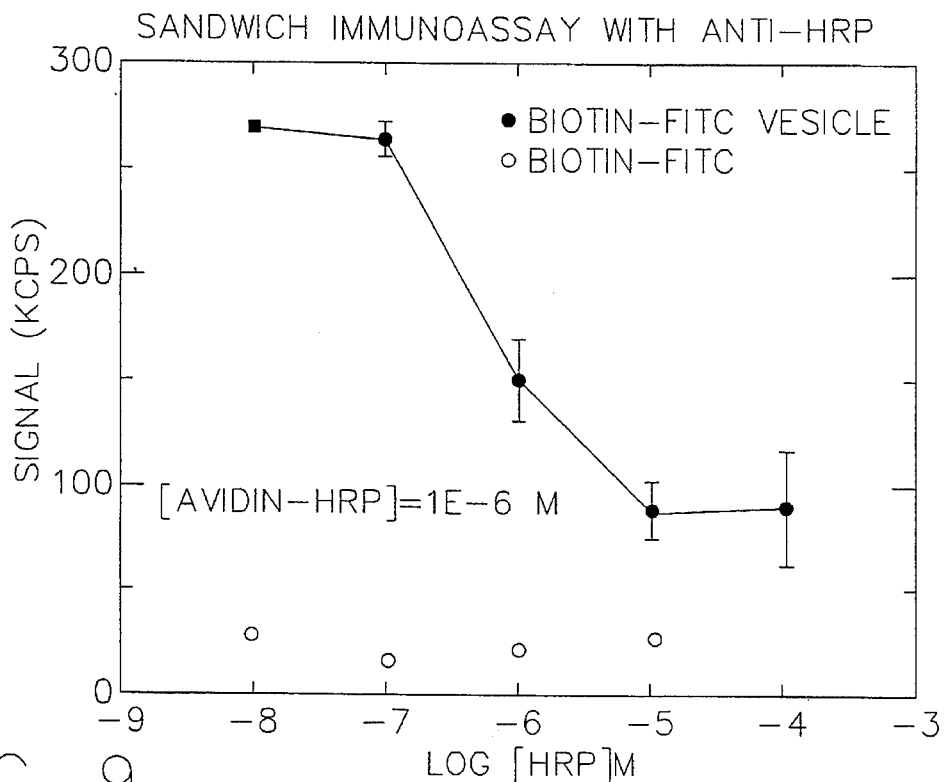
FIG. 9 shows the results of the sandwich immunoassay with anti-horseradish peroxidase (anti-HRP) described in Example 8.

The cuvettes previously described were incubated in 0.2 ml of 0.187 mg total protein/ml of polyclonal anti-horseradish peroxidase (anti-HRP) solution in phosphate buffered saline (PBS) for two hours at room temperature and was rinsed with 0.4 ml of PBS twice. The cuvettes were incubated in 0.2 ml of 3% bovine serum albumin (BSA) solution in PBS as a blocking agent for one hour at room temperature and were rinsed with 0.4 ml of PBS twice. The cuvettes were incubated in 0.2 ml of avidin-HRP solution having different concentrations of HRP ($10^{-9}$M to $10^{-4}$M) and were washed with 0.4 ml of PBS twice. The signal was measured with total internal reflection fluorescence using fluorescent biotin-conjugated liposomes at 0.1 mg/ml of total lipid and with FITC-biotin at $10^{-6}$M. The results are depicted in FIG. 9. The signal obtained with the vesicles in this assay were much larger than those obtained with biotin-FITC, primarily because the biotin-FITC was washed off the surface and the vesicles were not. The vesicles can be used in a sandwich immunoadsorbent assay with sufficient specificity. Levels of HRP of $10^{-8}$M can be detected with the protocol described above.

MATERIALS AND METHODS OF EXAMPLES 9–11

Materials

Horseradish peroxidase (HRP) type VI-A, affinity purified polyclonal anti-biotin antibody (ABA), affinity purified avidin, human immunoglobulin (IgG), 2,2' azinobis 3-ethylbenzthiazoline-6-sulfonic acid (ABTS), biotin, dimyristoyl phosphatidyl choline (DMPC), dimyristoyl phosphatidyl ethanolamine (DMPE), distearoyl phosphatidyl choline (DSPC), cholesterol, Sepharose CL 4B-200 and Sepharose CL 6B-200 were obtained from Sigma Chemical Company, St. Louis, Mo. Biotinyl-imidohexanoyl-N-hydroxysuccinimide ester or long chain biotin (biotin-LC-NHS) was obtained from Pierce Chemical Company, Rockford, Ill. All other chemicals were reagent grade or better.

Methods

Synthesis of DMPE-LC-Biotin

The biotinylated phospholipid was synthesized by coupling DMPE with biotin-LC-NHS using the method of Bayer and Wilcheck, Liposome Technology, Vol. 3, CRC Press, Boca Raton, Fla., 1984, pp. 127–135. DMPE (30 mg) and biotin-LC-NHS (25 mg) were dissolved in 2 ml of chloroform:methanol (2:1) by vortexing. After adding 20 μl triethylamine, the mixture was allowed to react at room temperature for two hours. DMPE-LC-biotin was purified by preparative thin-layer chromatography on silica gel plates (Analtech Inc., Newark, Del.) using chloroform:methanol:water (80:25:2) as the mobile phase. The product was identified using a cinnamaldehyde spray to detect biotin (McCormick and Roth, Methods in Enzymology, Vol. 18A, 1970, p. 383) and molybdenum spray to detect phospholipid (Dittmer and Lester, J. Lipid Res., 5, 1964, pp. 126–127). The silica gel containing DMPE-LC-biotin was removed from the plate and extracted with chloroform:methanol (2:1). After removal of the solvent on a rotary evaporator at 40° C., the product was weighed, dissolved in chloroform:methanol (2:1) and stored at −20° C. until use.

EXAMPLE 9

Liposomes were prepared by standard procedures (Szoka and Papahadjopoulos, Ann. Rev. Biophys. Biolsng., 9, 1980, 467). Briefly, 30 mg lipid was dissolved in chloroform:methanol (2:1) and dried in a rotary evaporator to form a thin lipid film on the inside wall of the flask. The lipids were then hydrated with 10 ml of 50 mM citrate buffer, pH 6.0. Unilamellar vesicles were formed by sonicating (Model W-385, Heat Systems Ultrasonics, Farmingdale, N.Y.) the hydrated lipid suspension above the phospholipid phase transition temperature. Undispersed phospholipid was removed by filtering the solution through a 0.2 μm Acrodisc filter (Gelman Sciences, Ann Arbor, Mich.).

Horseradish peroxidase was covalently linked to liposomes using the periodate method reported by Heath et al., Biochim. Biophys. Acta, 599, 42 (1980) with modification. Peroxidase (10 mg) in 1 CB, pH 6.0, was combined with 1 of 0.06M sodium periodate and allowed to react in the dark for thirty minutes, in which the periodate oxidizes the hydroxyl groups of the enzyme carbohydrate chains to aldehyde groups. Ethylene glycol (1 ml of 0.32M) was then added to the mixture and kept in the dark for one hour to neutralize excess periodate. After isolating the activated HRP on a desalting column (Econo-Pac 10DG, Bio-Rad Laboratories, Richmond, Calif.), liposomes were added and the pH adjusted to 9.5 and monitored for two hours. Under these conditions, the aldehydes react with the liposome surface amines to form an unstable imine intermediate. The imine was then converted to a stable covalent linkage by reduction with 2 mg borohydride. After incubating overnight at 25° C. the pH was adjusted to 6.0 before isolating the HRP-liposome conjugates.

The important features of the procedure that were varied in the four immobilization experiments, to be described in greater detail below, were (1) the HRP/phospholipid ratio used in the reaction mixture, (2) the method of isolating the HRP-liposome conjugates and (3) the liposome composition.

In the first immobilization, DMPC:cholesterol:DMPE (36:36:28) vesicles were used at an HRP/phospholipid ratio in the reaction mixture of 0.58 mg/μmol, and the HRP-liposome conjugates were isolated by diafiltration using an Amicon YM100 (100 kda MW cut off) membrane in a stirred cell. The diafiltration was stopped when no enzyme could be detected in the filtrate. In order to demonstrate that all of the free enzyme had been removed by diafiltration, the HRP-liposome conjugates were applied to a 1.5 cm×30 cm gel permeation chromatography (GPC) column with Sepharose CL 4B-200 (exclusion limit MW 20×10$^6$) packing at a flow rate of 1 ml/min, and 1 fractions were collected. The HRP activity and the phospholipid content was determined for the fractions.

In the second immobilization, the same vesicle composition as in the first case was used, but the HRP/phospholipid ratio was increased to 2.4 mg/μmol. Since GPC is faster and demonstrates the separation of vesicles from free enzyme more readily than diafiltration, the reaction mixture was fractionated using the same column and flow conditions described above. The HRP activity and phospholipid content the fractions were determined. In addition, the size of the conjugates in the fractions corresponding to the liposome peak was determined by QLS.

In the third immobilization, DSPC was used as the major phospholipid component, with an HRP/phospholipid ratio of 2.4 mg/μmol. The HRP-liposome conjugates were isolated on a 1.5 cm×70 cm GPC column with Sepharose CL 6B-200 (exclusion limit MW 4×10$^6$) packing at a flow rate of 0.5 ml/min, and 1 ml fractions were collected. The HRP activity and the size of the conjugates in the fractions corresponding to the liposome peak were determined by QLS. Fractions 32-41 were pooled and stored at 5° C.

In the fourth immobilization, biotinylated vesicles were used with an HRP/phospholipid ratio of 2.4 mg/μmol. The HRP/liposome conjugates were isolated on a 1.5 cm×70 cm GPC column with Sepharose CL 6B-200 packing at a flow rate of 0.5 ml/min, and 1 fractions were collected. The HRP activity of the fractions was determined. Fractions 33-42 were pooled and stored at 5° C.

After isolating the HRP-liposome conjugates, the immobilized enzyme concentration was calculated by measuring the rise above the absorbance due to the presence of liposomes at 400 nm and using the previously determined conversion factor of 0.56 (mg/ml)$A_{400}$.

The liposome solutions were prepared for QLS measurements by centrifuging 2 ml of the sample at 2000 rpm for fifteen minutes to force residual dust to the bottom of the borosilicate scattering cell. Measurements were performed at a 90 degree scattering angle using a Coherent Innova 70-3 argon-ion laser with a Brookhaven correlator and goniometer.

The phospholipid content was determined using a phosphate assay that relies on the complexation of inorganic phosphate with molybdenum (Bartlett, J. Biol. Chem., 234, 466, 1959). The phospholipid was first digested with ion $H_2SO_4$ for four hours at 160° C., to form inorganic phosphate. Next, a 0.22% ammonium molybdate solution and Fiske-Subbarow reagent (FSR) containing 1-amino-2-naphthol-4-sulfonic acid in 15% bisulfite was added and heated in a boiling water bath for ten minutes. The inorganic phosphate liberated in the digestion step reacts with the molybdate to form phosphomolybdic acid in the second heating step. This is then reduced by the FSR to form a stable blue color that can be detected spectrophotometrically at 830 nm. A standard curve was obtained using phospholipid.

Enzyme activity measurements were performed at on a Shimadzu 160-Model UV-visible spectrophotometer using the procedure outlined by Gallati, J. Clin. Chem. Clin. Biochem., 17, 1 (1979) with 2,2' azinobis 3-ethylbenzthiazoline-6-sulfonic acid (ABTS) and hydrogen peroxide as substrates at 25° C. First, 3 ml of 50 mM citrate buffer was pipetted into the sample and reference cuvettes and 100 μl aliquots of ABTS and $H_2O_2$ were added to the sample cuvette. Next, 10 μl enzyme solution was added to the sample cuvette with agitation, zeroed against buffer and the change in absorbance monitored with time at 410 nm. The HRP activity in the GPC fractions were obtained using 2 mM ABTS, 2.75 mM $H_2O_2$ at pH 4.2 Fractions containing high enzyme concentrations were diluted between 10 and 100 times to obtain ΔA/min values and the activity of the reported fraction was calculated based on the dilution. Activity measurements to obtain kinetic parameters were performed at a fixed hydrogen peroxide concentration (2.75 mM) and various ABTS concentrations for pH values ranging from 3.5 to 6.0. Kinetic parameters were determined graphically using the double reciprocal plot of Lineweaver-Burk for HRP on liposomes isolated in immobilizations 1, 3 and 4. In addition, kinetic parameters were obtained for free enzyme.

Two control experiments were performed to determine the extent of non-specific binding of HRP to liposomes. In the first experiment, DMPC:cholesterol (50:50) liposomes were substituted for liposomes containing phosphatidyl ethanolamine in the immobilization procedure outlined earlier and fractionated by GPC. In the second control experiment, DSPC:cholesterol:DSPE (36:36:28) vesicles were incubated at pH 9.5 with HRP that had not been activated with periodate and fractionated by GPC.

EXAMPLE 10

This Example sets forth a procedure for forming horseradish peroxidase (HRP) conjugated liposomes, or vesicles, and their use in accordance with the present invention.

Materials Used

Horseradish peroxidase (HRP) type VI-A, affinity purified polyclonal anti-biotin antibody (ABA), affinity purified avidin, 2,2' azinobis 3-ethylbenzthiazoline-6-sulfonic acid (ABTS), biotin, dimyristoyl phosphatidylchotine (DMPC), dimyristoyl phosphatidyl ethanolamine (DMPE), distearoyl phosphatidylcholine (DSPC), cholesterol, and SEPHAROSE CL 6B-200 were obtained from Sigma Chemical Company, St. Louis, Mo. Biotinyl imidohexanoyl-N-hydroxysuccinimide ester or long chain biotin (biotin-LC-NHS) was obtained from Pierce Chemical Company, Rockford, Ill. All other chemicals from were reagent grade or better.

Methods Used

Synthesis of DMPE-LC-Biotin

The biotinylated phospholipid was synthesized by coupling DMPE with biotin-LC-NHS using the following procedure of Bayer et al., cited in Example 1: DMPE (30 mg) and biotin-LC-NHS (25 mg) were first dissolved in 2 ml of chloroform:methanol (2:1) by vortexing. After adding 20 μl of triethylamine, the mixture was allowed to react at room temperature for two hours. DMPE-LC-biotin was purified by preparative thin-layer chromatography on silica gel plates (Analtech Inc., Newark, Del.) using chloroform:methanol:water (80:25:2) as the mobile phase. The product was identified using a cinnamaldehyde spray to detect biotin (McCormick et al., cited in Example 1) and a molybdenum spray to detect phospholipid (Dittmer et al., cited in Example 1). The silica gel containing DMPE-LC-biotin was removed from the plate and was extracted with chloroform:methanol (2:1). After removal of the solvent on a rotary evaporator at 40° C., the product was dissolved in chloroform:methanol (2:1) and was stored at −200° C. until use.

Vesicle Preparation

Vesicles were prepared by standard procedures (Szoka et al., cited in Example 9). Briefly, 30 mg lipid was dissolved in chloroform:methanol (2:1) and was dried in a rotary evaporator to form a thin lipid film on the inside wall of the flask. The lipids were then hydrated in 10 ml of 50 mM citrate buffer pH 6.0. Unilamellar vesicles were formed by sonicating (Model W-385 apparatus, Heat Systems Ultrasonics, Farmingdale, N.Y.) the hydrated lipid suspension above the phospholipid phase transition temperature. Undispersed phospholipid was removed by centrifuging at 5000 rpm for twenty minutes and filtering the solution through a 0.2 μm Acrodisc filter (Gelman Sciences, Ann Arbor, Mich.).

HRP Immobilization and Isolation

Horseradish peroxidase was covalently linked to vesicles using the periodate method reported by Heath et al., cited in Example 9, with modification. Peroxidase (50 mg) in 5 ml of 50 mM citrate buffer, pH 6.0, was combined with 5 ml of 0.06M sodium periodate and was allowed to react in the dark for thirty minutes, in which the periodate oxidizes the hydroxyl groups of the enzyme carbohydrate chains to aldehyde groups. Ethylene glycol (5 ml of 0.32M) was then added to the mixture and kept in the dark for one hour to neutralize excess periodate. After isolating the activated HRP on a desalting column (Econo-Pac 10DG, BioRad laboratories, Richmond, Calif.), 5 ml of 3 mg/ml vesicles were added, and the pH was adjusted to 9.5 and was monitored for two hours. Under these conditions, the aldehydes reacted with the vesicle surface amines to form an unstable imine intermediate. The imine was then reduced to a stable covalent linkage by adding 2–3 mg sodium borohydride followed by incubation overnight at 250° C. The pH was then adjusted to 6.0, and the reaction mixture was concentrated to 2 ml using an Amicon Centriprep-10 concentrator. The resulting reaction mixture was applied to a 1.5 cm×70 cm SEPHAROSE CL-6B (exclusion limit: MW 4×106) gel permeation chromatography (GPC) column and was eluted with 50 mM CB pH 6.0 at a flowrate of 0.5 ml/min.

Characterization Of Immobilized HRP

After isolating the HRP-vesicle conjugates, the immobilized enzyme concentration was calculated by measuring the rise above the absorbance due to the presence of vesicles at 400 nm and using a previously determined conversion factor of 0.56 (mg/ml)/A400.

The vesicle solutions were prepared for QLS measurements by centrifuging 2 ml of the sample at 2000 rpm for fifteen minutes to force residual dust to the bottom of the borosilicate scattering cell. Measurements were performed at a 90 degree scattering angle using a Coherent Innova 70-3 argon-ion laser with a Brookhaven correlator and goniometer.

The phospholipid analysis was performed as follows: Briefly, 100 μl of sample containing between 0.025 and 0.25 μmol phosphorous was heated to 250° C. with 500 μl of 10N sulfuric acid for twenty minutes. After cooling to room temperature, six drops of low-phosphate 30% hydrogen peroxide were added to each sample which was and reheated to 250° C. for thirty minutes. After cooling, 3.9 ml deionized water, 0.5 ml of 2.5%, and 0.5 ml 10%, ascorbic acid were added to each sample which was then heated in a boiling waterbath for seven to ten minutes. After cooling, the absorbance at 830 nm for the samples was measured on a Shimadzu 160-Model UV-visible spectrophotometer. A calibration curve was obtained using phospholipid and standard inorganic phosphate solutions. Enzyme activity measurements were performed at on a Shimadzu 160-Model UV visible spectrophotometer using the procedure outlined by Gallati, cited in Example 9 in 50 mM citrate buffer with 2,2' azinobis 3-ethylbenzthiazoline-6-sulfonic acid (ABTS) and hydrogen peroxide as substrates at 25° C. First, 3 ml of buffer was pipetted into the sample and reference cuvettes and 100 μl aliquots of ABTS and hydrogen peroxide were added to the sample cuvette. Next, 10 μl of enzyme solution was added to the sample cuvette with agitation, zeroed against buffer and the change in absorbance was recorded at 410 nm. The HRP activity in the GPC fractions were measured using 2 mM ABTS, 2.75 mM hydrogen peroxide at pH 4.0. Fractions containing high enzyme concentrations were diluted between 10 and 100 times to obtain AA/min values and the activity of the reported fraction was calculated based on the dilution. Activity measurements to obtain kinetic parameters were performed at a fixed hydrogen peroxide concentration (2.75 mM) and various ABTS concentrations at pH values ranging from 3.5 to 5.0. Kinetic parameters were determined using a non-linear least-squares fitting technique. The optimum activity was near pH 4.0 with 2.0 mM ABTS.

The kinetic activity-specific activity of the immobilized enzyme was 65% of the free enzyme activity.

| pH  | $K_m$ (free) | $K_m$ (imm) | $k_p \times 10^{-5}$ (free) | $k_p \times 10^{-5}$ (imm) |
|-----|--------------|-------------|------------------------------|-----------------------------|
| 3.5 | 0.085        | 0.079       | 0.60                         | 0.39                        |
| 3.8 | 0.141        | 0.138       | 0.94                         | 0.64                        |
| 4.0 | 0.178        | 0.193       | 0.93                         | 0.66                        |
| 4.2 | 0.208        | 0.248       | 0.87                         | 0.65                        |
| 4.5 | 0.274        | 0.296       | 0.70                         | 0.53                        |
| 5.0 | 0.304        | 0.349       | 0.32                         | 0.27                        |

$K_m$ [=] mM
$k_p$ = Vmax/[HRP] [=] (ΔA/min)/(mg/ml)

In two separate batches, the average diameter was 1010 and 870 Å, respectively, the HRP/vesicle ratios were 171 and 137, respectively, and the biotin/vesicle ratios were 1400 and 1000, respectively.

Two control experiments were performed to determine the extent of non-specific binding of HRP to vesicles. In the first experiment, DMPC:cholesterol (50:50) vesicles were substituted for vesicles containing phosphatidylethanolamine in the immobilization procedure outlined earlier and fractionated by GPC. In the second control experiment, DSPC:cholesterol:DSPE (36:36:28) vesicles were incubated at pH 9.5 with HRP that had not been activated with periodate and fractionated by GPC. Vesicles conjugated with both HRP and biotin will be subsequently referred to as HBVs.

Total ABA per unit area on polystyrene wells

Figure 10:
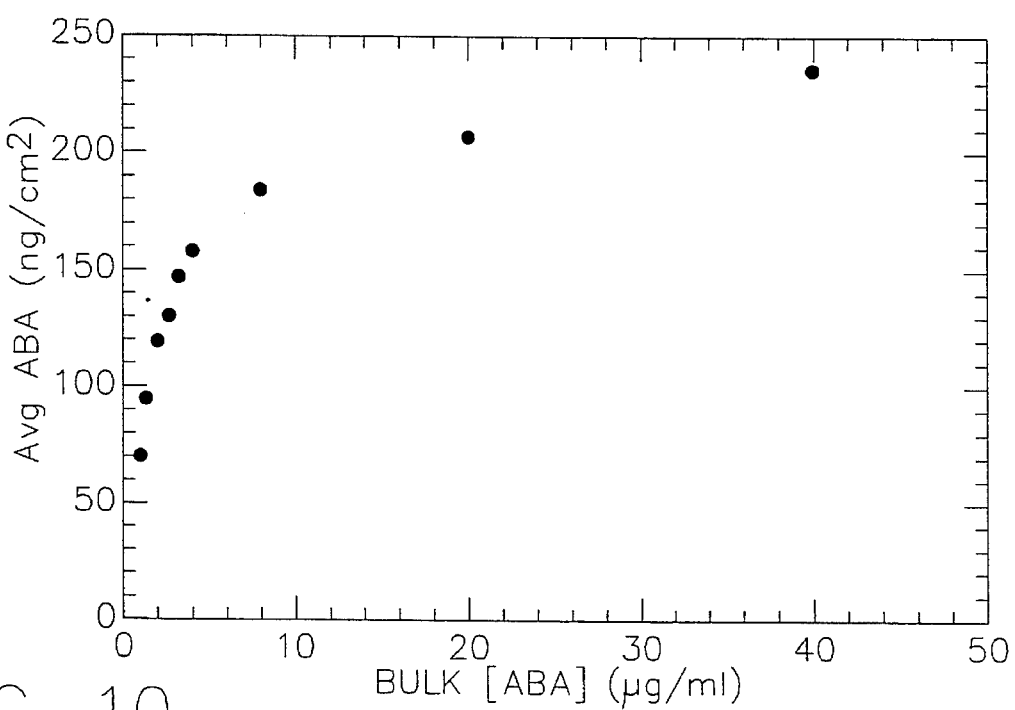
FIG. 10 shows the total anti-biotin antibody (ABA) adsorbed to polystyrene microplates per area.

The total antibody adsorbed to the well face was determined using radiolabeled ABA. First, the antibody was radiolabel with 14-C formaldehyde using the reductive alkylation method outlined by Jenthoff, et al., cited in Example 2. ABA was adsorbed to the wells by incubating 200 μl of ABA solution (40-1 μl/ml) in PBS for two hours at 250° C. After rinsing three times with PBS, the wells were immersed in a scintillation cocktail and analyzed on a PAKDARD 1500 liquid scintillation counter. The total amount of ABA adsorbed per unit area was calculated from the antibody specific radioactivity and the manufacturersupplied area of 1.41 cm² per well at a well volume of 200 μl. FIG. 10 illustrates the average ABA (ng/cm²) per bulk ABA (μg/ml) with $\Gamma_{max}=236\pm27$ ng/cm².

HBV and B-HRP Adsorption to ABA-coated PS Wells

The wells were coated with antibody as in the previous section. Next, the wells were blocked by incubation with 200 μl of 1 wt % BSA in PBS for one hour at room temperature, followed by rinsing three times with 300 μl aliquots of PBS. Additional wells were simply blocked with BSA to determine the extent of non-specific binding. Aliquots of HBVs or B-HRP (100 μl) were added to the wells and were allowed to bind. The HBV incubation time was two hours, while the B-HRP incubation time was one hour. After removing the incubating solution the wells were washed with PBS. The wells containing HBVs were rinsed four times with 300 μl aliquots of buffer, while the wells containing B-HRP were rinsed twice with 100 μl additions of buffer. Next, 100 μl of substrate solution was added to each well. For HBVs 2 mMABTS with 2.75 mM hydrogen peroxide in CB, pH 5.0, was used, while 0.5 mMABTS with 2.75 mM hydrogen peroxide in CB, pH 4.0, was used for B-HRP. The ΔA/min values were measured on a Biotek EL 340 platereader at 410 nm.

Figure 11:
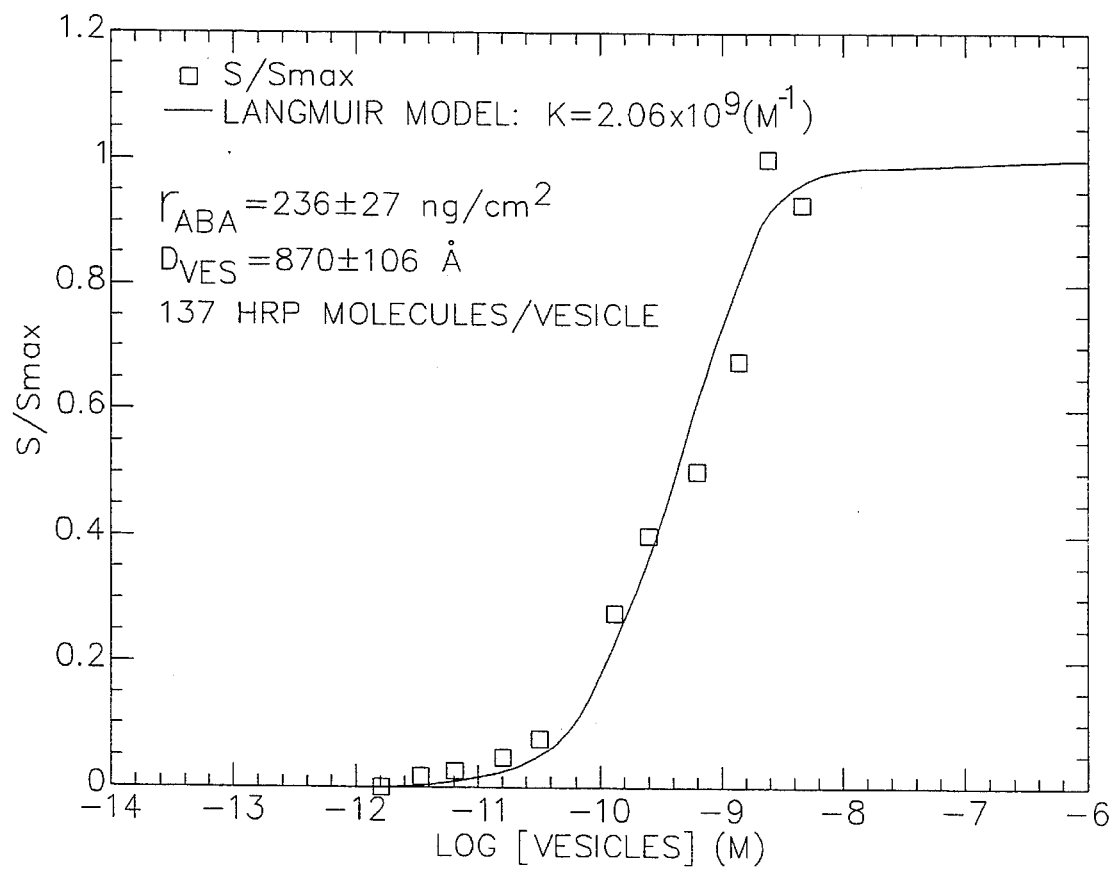
FIG. 11 is the adsorption isotherm of horseradish peroxidase-conjugated and biotin-conjugated vesicles (HBVs) onto an ABA monolayer.

The adsorption isotherm of HBVs onto the ABA monolayer is set forth in FIG. 11.

The Table set forth below gives a summary of the binding coefficients for HBVs on adsorbed ABA:

| HBV Batch No. | $\Gamma_{ABA}$(fraction) | K(nM$^{-1}$) |
| --- | --- | --- |
| 1 | 0.95 | 7.2 |
| 1 | 0.80 | 6.2 |
| 1 | 0.67 | 8.3 |
| 1 | 0.51 | 10.2 |
| 2 | 0.95 | 2.1 |
| 2 | 0.49 | 6.0 |

Figure 12:
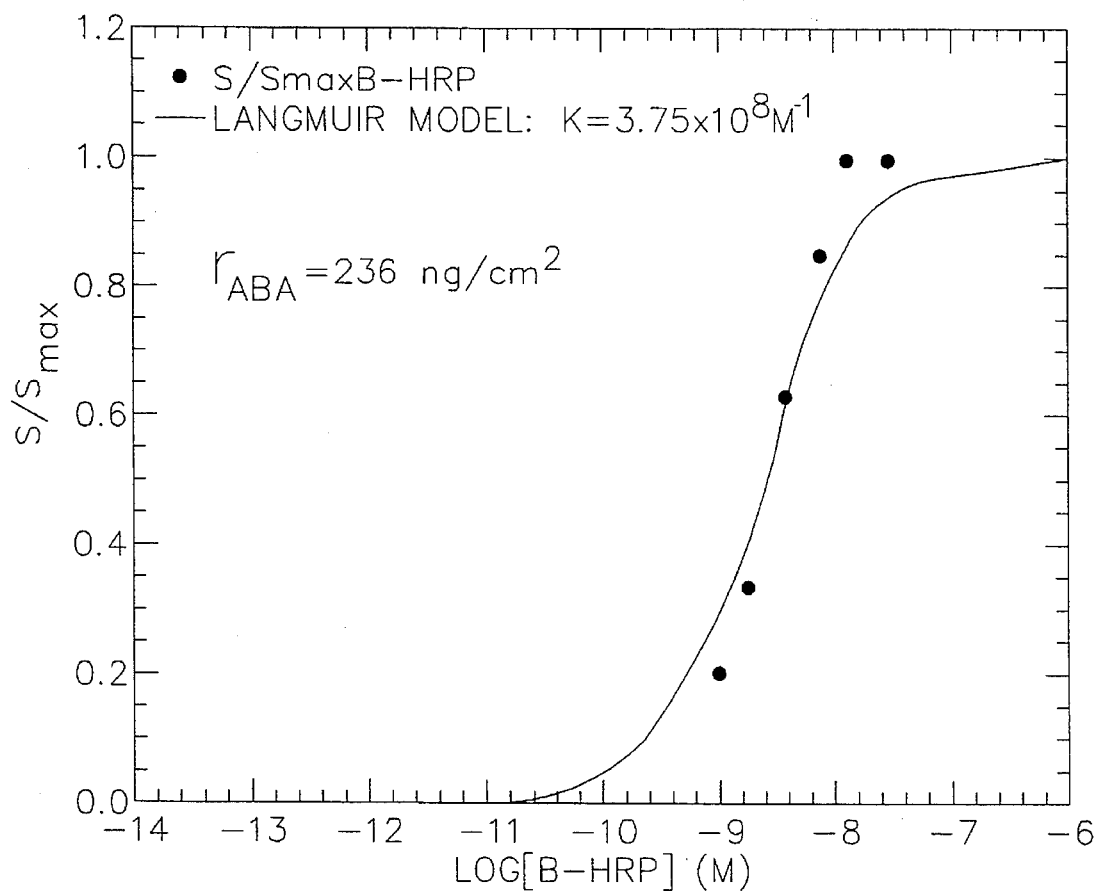
FIG. 12 is the adsorption isotherm for biotinylated horseradish peroxidase (biotin-HRP) to an ABA monolayer.

The adsorption equilibrium constant for biotin-HRP to the ABA monolayer is set forth in FIG. 12.

Competitive Assay for Biotin Using HBVs

Polystyrene microtiter plates were coated with ABA by using 200 μl of ABA solution (40 μg/ml to1 μg/ml) per well in PBS at a pH of 7.4. The solution was allowed to remain for two hours at 25° C. and was then rinsed twice with PBS, pH of 7.4.

The wells were than blocked with 200 μl of a 1 wt % solution of BSA per well which solution was allowed to remain for one hour at 25° C. followed by rinsing three times with PBS, pH of 7.4.

The system was then incubated with 100 μl of a solution of biotin and HBVs for each well. The biotin was between $10^{-4}$ and $10^{-14}$M. The solution was allowed to remain for two hours at 25° C. and was rinsed four times with PBS, pH of 7.5.

Then, the substrate (100 μl of 2 mMABTS, 2.75 mM hydrogen peroxide per well in 50 mM citrate buffer, pH of 4.0) was added.

Figure 13:
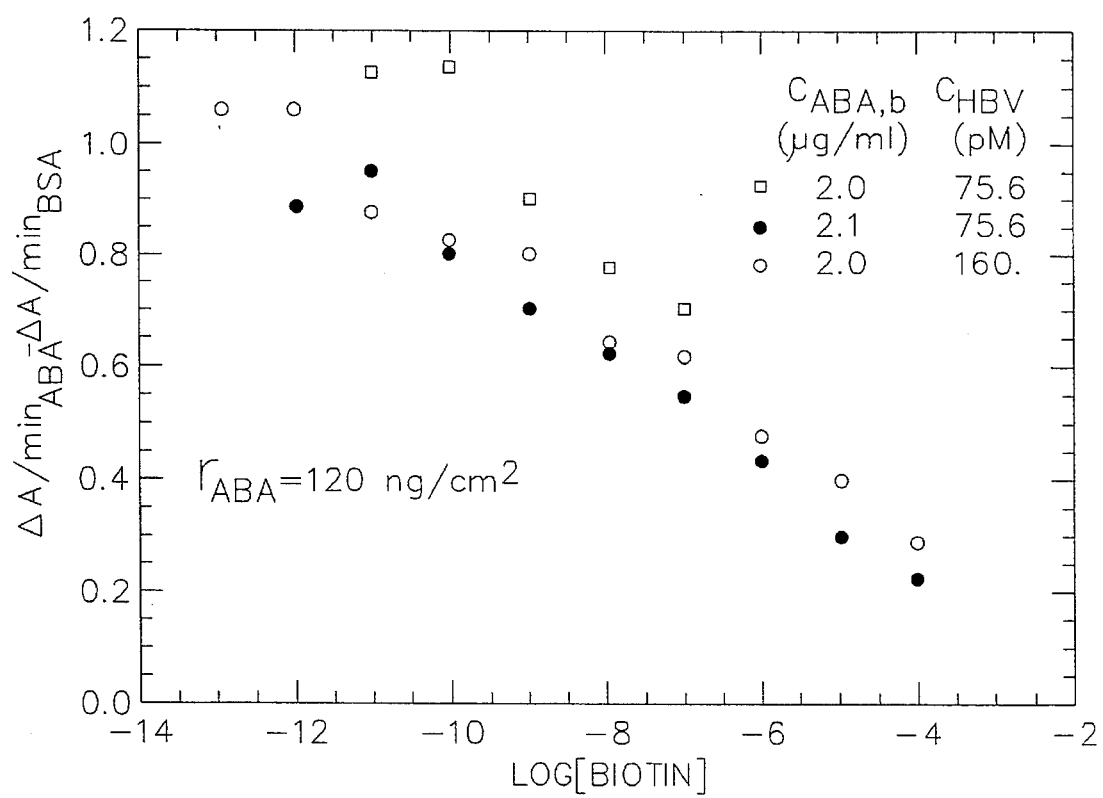
FIG. 13 shows the results of a competitive assay for biotin using HBVs (50% monolayer)

FIG. 13 sets forth the results of the competitive assay for biotin using HBVs (50% monolayer).

Competitive Assay for Biotin Using B-HRP

Polystyrene microtiter plates were coated with ABA using the same procedure described above in the competitive assay using HBVs. The wells were then blocked with BSA using the same procedure as in the assay using HBVs.

The plates were then incubated with a biotin/B-HRP solution (100 μl of solution per well, biotin=$10^{-4}$ to $10^{-14}$M) for one hour at 25° C. and rinsed twice with PBS, pH of 7.4.

Figure 14:
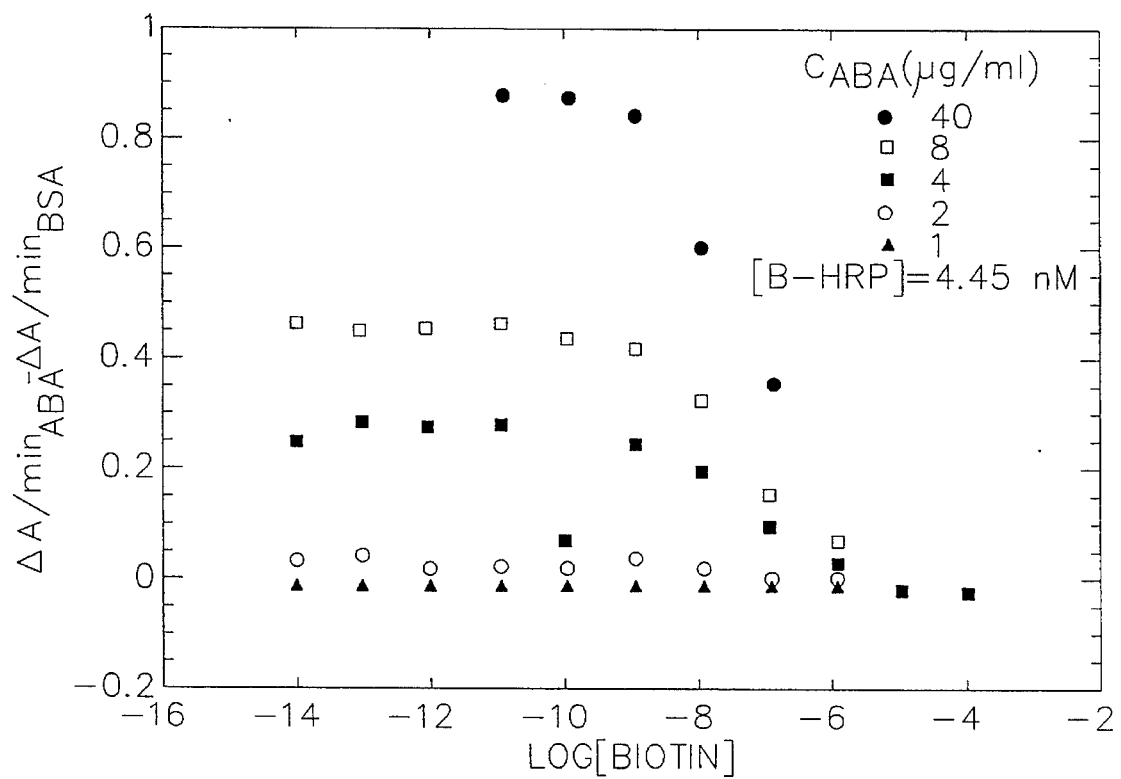
FIG. 14 shows the results of a competitive assay for biotin using biotin-HRP.

Substrate (100 μl of 0.5 mM ABTS and 2.75 mM hydrogen peroxide per well in 0.50 mM citrate buffer, pH of 4.0) was then added. FIG. 14 shows the results of this competitive assay.

A comparison of FIG. 14 with FIG. 13 shows that the vesicle assay is able to detect free biotin concentrations on the order to $10^{-12}$M while, under the best conditions, the B-HRP assay can detect biotin beginning at $10^{-9}$M. The vesicle adsorption is more sensitive to the presence of free antigen than the single-labeled HRP possibly due to multiple-binding site interaction between vesicles and the surface. It is also apparent that the same ABA surface coverage (50%), the signal obtained from the vesicles is significantly larger than the signal obtained from the B-HRP. This demonstrates that for a low number of surface sites on the solid, the vesicles gave much superior signals signifying that vesicles can be utilized to obtain higher measurement sensitivity.

EXAMPLE 11

This Example illustrates the preparation of novel liposomes, or vesicles, with covalently attached horseradish peroxidase and antibodies.

The general methods used for making these vesicles, carrying out the reaction, and characterizing the vesicles is the same as described in Example 8. The vesicles were formed by sonication of DSPC:Cholesterol:DMPE (40:40:20) followed by sequential reaction of the proteins (3 mg HRP/mg vesicles, isolation of vesicles (HV) by GPC and [$^{14}$C]-anti-bovine albumin (ABA) with HV at 1 mg antibody to HV, isolation of HAVs by GPC). The antibody/enzyme labeled vesicles (HAVs) were then characterized: quasi-elastic light scattering (about 1100 Å, average size, as compared to about 600 Å for the original vesicles and 780 Å for the HAVs), radioactivity (about 8–19 antibody molecules per vesicle), and about 114–262 enzymes per vesicle. The reaction of ABA with HVs gave precipitation upon concentration with a 14% recovery of vesicles based on phospholipid recovery.

Figure 15:
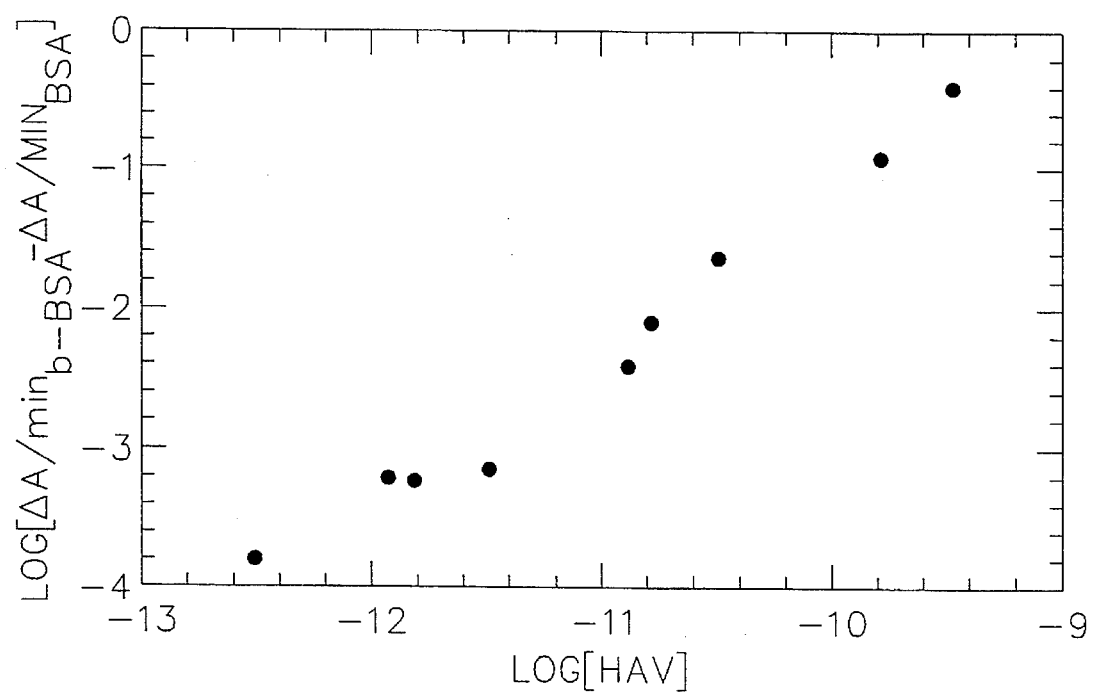
FIG. 15 shows the isotherms for the adsorbance of antibody and enzyme labeled vesicles (HAVs) to a biotin-coated surface.

The HAVS were specifically bound to a biotinylated surface by first coating polystyrene microtiter plates by incubating 200 μl of 40 μg/ml biotin-(LC)-bovine serum albumin (BSA) overnight at 4° C. and rinsed twice with PBS at a pH of 7.4. The wells were blocked with 200 μl of 1 wt % BSA for one hour at 25° C. Additional wells were also coated with BSA for determining the non-specific signal and were rinsed three times with PBS. The wells were then incubated with 100 μl of various HAV concentrations for two hours at 25° C. and were rinsed four times with PBS. Then, 100 μl of substrate (2.0 mM ABTS and 2.75 mM hydrogen peroxide) in 50 mM citrate buffer, pH 4.0, was added. The isotherms to the biotin-BSA coated plates is shown in FIG. 15. The background signal was between 20%–50%.

We claim:

1. A competitive immunodiagnostic assay for determining the amount of an unknown antigen or antibody, respectively, in a sample comprising:

(a) contacting the sample with:

(a) a plurality of immobilized antibodies or antigens, respectively, bonded to a solid support and in contact with a solution; and carrying (A) a plurality of labels which are covalently bonded to the outer surface of each liposome, and (B) at least one antigen or antibody, respectively, also covalently bonded to the outer surface of each liposome, wherein the ratio of labels to antigens or antibodies bonded to the outer surface of a single liposome is between about 412:1 and about 1650:1 and wherein said covalently bonded antigen or antibody and said unknown antigen or antibody are each complimentary to the immobilized antibodies or antigens, respectively, so that said covalently bonded antigen or antibody and said unknown antigen or antibody compete to bind with said immobilized antibodies or antigens so as to bind the liposomes to at least one immobilized antibody or antigert, respectively, on the support; and (b) detecting the labels adjacent the support without rupture of the liposomes thereby providing a competitive measurement of the amount of unknown antigen or antibody in the sample.

2. An assay as claimed in claim 1 wherein the label is a detectible marker which is visually or spectrophotometrically detectible.

3. An assay as claimed in claim 2 wherein the detectible marker is a fluorophore.

4. An assay as claimed in claim 1 wherein the label is a catalyst for a detectible marker and is an enzyme.

5. An assay as claimed in claim 1 wherein the support is a transparent waveguide adapted when illuminated to generate an evanescent wave in the solution adjacent the waveguide and the label is one which is detectible thereby.

6. A two-site immunodiagnostic assay for determining the amount of an unknown antigen or antibody, respectively, in a sample comprising:

(a) contacting the sample with:
(i) a plurality of immobilized antibodies or antigens, respectively, bonded to a solid support which are complementary to the unknown antigen or antibody, respectively, and which are in contact with the solution; and (ii) a plurality of unilamellar liposomes carrying (A) a plurality of labels which are covalently bonded to the outer surface of each liposome, and (B) at least one antigen or antibody, respectively, also covalently bonded to the outer surface of each liposome, which is also complementary to the unknown antigens or antibodies, respectively, wherein the ratio of labels to antigens or antibodies bonded to the outer surface of a single liposome is between about 412:1 and about 1650:1 so as to indirectly bind the liposomes to the immobilized antibodies or antigens, respectively, on the support with the unknown antigen or antibody lying therebetween; and (b) detecting the labels adjacent the support without rupture of the liposomes thereby providing a direct measurement of the amount of unknown antigen or antibody in the sample.

7. An assay as claimed in claim 6 wherein the label is a detectible marker which is visually or spectrophotometrically detectible.

8. An assay as claimed in claim 7 wherein the detectible marker is a fluorophore.

9. An assay as claimed in claim 6 wherein the label is a catalyst for a detectible marker and is an enzyme.

10. An assay as claimed in claim 6 wherein the support is a transparent waveguide adapted when illuminated to generate an evanescent wave in the solution adjacent the waveguide and the label is one which is detectible thereby.

11. A unilamellar liposome, which comprises lipid wall portions having directly attached thereto, on the outer wall surface thereof, (i) at least one antigen or antibody, adapted to allow for either (a) the immobilization of the liposome adjacent to a solid support by direct bonding to immobilized antibodies or antigens, respectively, on the solid support or (b) the immobilization of the liposome adjacent to a solid support by indirect bonding to immobilized antigens or antibodies, respectively, on the solid support via an intermediately disposed complementary antibody or antigen, and (ii) a plurality of labels also directly attached to the outer wall surface of the liposome, wherein the ratio of labels to antigens or antibodies bonded to the outer surface of the liposome is between about 412:1 and about 1650:1, and wherein said labels are detectable markers detectable when the liposome is immobilized adjacent to the solid support in response to an antibody-antigen reaction so as to thereby provide a measurement of an unknown antibody or antigen in bulk solution in either a competitive or sandwich-type assay procedure.

12. A liposome as claimed in claim 11 wherein the detectible marker is visually or spectrophotometrically detectible.

13. An assay as claimed in claim 6 wherein said assay is a sandwich assay.

14. A kit for measuring the amount of an unknown ligand in a bulk solution, comprising:

(a) a solid support means comprising a plurality of immobilized anti ligands complimentary to said unknown ligand; and (b) a plurality of unilamellar liposomes carrying (i) a plurality of detectable markers covalently bonded to the outer surface of each liposome and (ii) at least one ligand also covalently bonded to the outer surface of each liposome wherein said ratio of detectable markers to ligand is between about 412:1 and about 1650:1, and wherein said covalently bonded ligand is complimentary to said immobilized anti ligands so that said covalently bonded ligand and said unknown ligand compete to bind with said immobilized anti ligands so as to bind the liposomes to at least one immobilized antiligand on the solid support and allow for the detection of the labels adjacent the solid support.

15. An assay as claimed in claim 1, wherein said liposomes are between about 570Å and about 1010Å in diameter.

16. An assay as claimed in claim 6, wherein said liposomes are between about 570Å and about 1010Å in diameter.

17. A liposome as claimed in claim 11, wherein the detectible marker is an enzyme.

18. A liposome as claimed in claim 11, wherein said iposome is between about 570Å and about 1010Å in diameter.

* * * * *

UNITED STATES PATENT AND TRADEMARK OFFICE
CERTIFICATE OF CORRECTION

PATENT NO. : 5,494,803  
DATED : 27 February 1996  
INVENTOR(S) : Ruben G. Carbonell, Peter K. Kilpatrick, Matthew A. Jones, Anup K. Singh It is certified that error appears in the above-identified patent and that said Letters Patent is hereby corrected as shown below:

Column 8, line 34, please add -- ml -- after 1.

Column 8, line 61, please delete the bold on " $10^{-4}$ ".

Column 9, line 56, please correct "1 /min" to read -- 1 ml/min --

Column 10, line 31, please correct "PE" to read -- PMMA --.

Column 10, formula 1, please correct "$Ab_{(s)}+L\ AbL_{(s)}$" to read -- $Ab_{(s)}+L \longleftrightarrow AbL_{(s)}$ --.

Column 11, line 22, please correct "FAbL" to read -- $\Gamma_{AbL}$ --.

Column 11, formula 5, please correct "$_{Ab\ o}$" to read -- $_{Ab°}$ --.

Column 17, line 51, please correct "OF" to read -- FOR --.

Column 18, line 42, please correct both "1" to read -- 1 ml --.

Column 19, lines 8 and 34, please correct "1" to read -- 1 ml --

Column 19, line 53, please correct "ion" to read -- 1ON --.

Column 21, line 50, please correct "A400" to read -- $A_{400}$ --.

Column 22, line 18, please correct "AA/" to read -- $\Delta A$ --.

Column 22, line 28, please correct "65%" to read --65% to 80%--.

Column 23, line 3, please correct "236±27" to read --236+/27--.

UNITED STATES PATENT AND TRADEMARK OFFICE
CERTIFICATE OF CORRECTION

PATENT NO. : 5,494,803            Page 2 of 2
DATED : 27 February 1996
INVENTOR(S) : Ruben G. Carbonell, Peter K. Kilpatrick, Matthew A. Jones, Anup K. Singh It is certified that error appears in the above-identified patent and that said Letters Patent is hereby corrected as shown below:

Column 23, lines 19, 20 and 54, please correct "mMABTS" to read --mM ABTS--.

Column 23, line 41, please correct "to1" to read --to 1--.

Column 24, line 62, please correct "(a)" to read --(i)--.

Column 24, line 64, please insert --(ii) a plurality of unilamellar liposomes-- after and.

Column 26, claim 14, lines 33, 43 and 45, please correct "anti ligands" to read --antiligands--.

Column 26, claim 18, line 58, please correct "iposome" to read --liposome--.

Signed and Sealed this

Second Day of July, 1996

*Attest:*

BRUCE LEHMAN

*Attesting Officer*      *Commissioner of Patents and Trademarks*